United States Patent [19]

Behling et al.

[11] Patent Number: 5,840,961

[45] Date of Patent: Nov. 24, 1998

[54] ASYMMETRIC SYNTHESIS OF CHIRAL BETA-AMINO ACIDS

[75] Inventors: James Richard Behling, Lindenhurst; Mark Laurence Boys, Mt. Prospect; Kimberly Jo Cain-Janicki, Sleepy Hollow; Pierre-Jean Colson, Skokie, all of Ill.; Wendel William Doubleday, Encinitas, Calif.; Joseph Edward Duran, Chicago, Ill.; Payman N. Farid, Vernon Hills, Ill.; Carl Matthew Knable, Mt. Prospect, Ill.; Frank Walter Muellner, Hinsdale, Ill.; Sean Thomas Nugent, Grayslake, Ill.; Ravindra S. Topgi, Palatine, Ill.

[73] Assignee: G. D. Searle & Co., Chicago, Ill.

[21] Appl. No.: 890,907

[22] Filed: Jul. 10, 1997

Related U.S. Application Data

[60] Provisional application No. 60/021,631 Jul. 12, 1996.

[51] Int. Cl.$^6$ .................................................. C07C 229/00
[52] U.S. Cl. .................. 560/172; 546/329; 549/494; 560/39; 560/35; 556/413; 556/418
[58] Field of Search ..................... 560/172, 39; 546/329; 549/494

[56] References Cited

U.S. PATENT DOCUMENTS

| 5,344,957 | 9/1994 | Bovy et al. ................................ 560/35 |
| 5,536,869 | 7/1996 | Babiak et al. ............................. 560/35 |
| 5,631,399 | 5/1997 | Babiak et al. ............................ 560/155 |

OTHER PUBLICATIONS

Hua et al. "Synthesis of 4–Substituted 2–Azetidinones", *Tetrahedron Letters,* vol. 26, No. 5, pp. 548–550, (1985).

Tetsuji Kametani "Synthesis of Carbapenem Antibiotics," *Heterocycles,* vol. 17, 463–506, (1982).

Andrés et al. "Stereoselective Ring Opening of Chiral Oxazolidines by Reformatsky Reagents: An Enantioselective Entry to β–Amino Esters," *Tetrahedron Letters,* vol. 33, 2895–2898, (1992).

Mokhallalati et al. "An Efficient Enantiomeric Three Step Synthesis of β–Amino Acids (Esters)" *Tetrahedron Letters,* vol. 34, No. 1, pp. 47–50, 1993.

*Primary Examiner*—Michael L. Shippen
*Attorney, Agent, or Firm*—Cynthia S. Kovacevic

[57] ABSTRACT

The invention herein is directed to a process for the preparation of ethyl 3S-amino-4-pentynoate which involves treating 3-(trimethylsilyl)-2-propynal with L-phenylglycinol in toluene to produce αS-[[3-(trimethylsilyl)-2-propynylidene amino]benzenethanol; reacting αS-[[3-(trimethylsilyl)-2-propynylidene]amino]benzenethanol with BrZnCH$_2$CO$_2$t-Bu in THF/NMP to produce 1,1-dimethylethyl 3S-[(2-hydroxy-1S-phenylethyl)amino]-5-(trimethylsilyl)-4-pentynoate; reacting the 1,1-dimethylethyl 3S-[(2-hydroxy-1S-phenylethyl)amino]-5-(trimethylsilyl)-4-pentynoate with sodium periodate to form 1,1-dimethylethyl 3S-[(phenylmethylene)amino]-5-(trimethylsilyl)-4-pentynoate; hydrolyzing 1,1-dimethylethyl 3S-[(phenylmethylene)amino]-5-(trimethylsilyl)-4-pentynoate to produce 1,1-dimethylethyl 3S-amino-5-(trimethylsilyl)-4-pentynoate; transesterifying 1,1-dimethyl 3S-amino-5-(trimethylsilyl)-4-pentynoate and desilylating to produce ethyl 3S-amino-4-pentynoate.

19 Claims, No Drawings

ASYMMETRIC SYNTHESIS OF CHIRAL BETA-AMINO ACIDS

This application claims the benefit of U.S. provisional application Ser. No. 60/021,631 filed Jul. 12, 1996.

BACKGROUND OF THE INVENTION

The present invention relates to a process for the preparation of chiral beta-amino acids of the formula

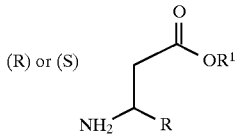

wherein R is selected from the group consisting of alkenyl, alkynyl, lower alkyl, aryl, substituted aryl, pyridyl, and furanyl and $R^1$ is lower alkyl; which process comprises treating an aldehyde of the formula

with (R) or (S) phenylglycinol in tetrahydrofuran (THF) or toluene to produce an imino alcohol of the formula

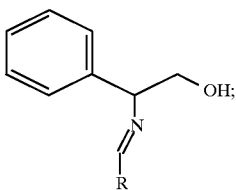

reacting said imino alcohol with $BrZnCH_2CO_2$-tBu in N-methyl pyrrolidinone (NMP), dimethylsulfoxide (DMSO) or THF followed by addition of aqueous ammonium chloride and hydrochloric acid to produce an amino alcohol of the formula

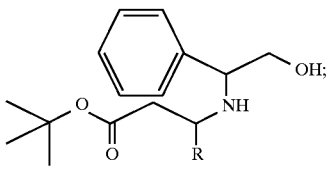

reacting the amino alcohol with sodium periodate ($NaIO_4$) or lead tetraacetate ($Pb(OAc)_4$) to form an imine of the formula

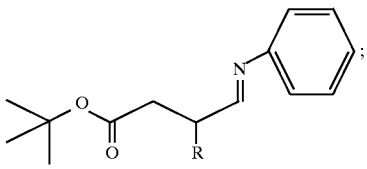

hydrolyzing said imine in the presence of para toluene sulfonic acid to produce an (R) or (S) beta-amino acid of the formula

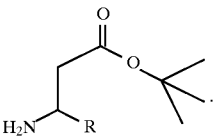

More preferably, the present invention relates to a process for the preparation of the chiral beta-amino acid of the formula

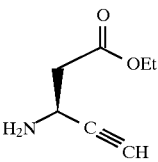

known by the chemical name ethyl 3S-amino-4-pentynoate and salts thereof. The process comprises treating 3-(trimethylsilyl)-2-propynal with L-phenylglycinol in toluene, to produce αS-[[3-(trimethylsilyl)-2-propynylidene]amino]benzenethanol; reacting αS-[[3-(trimethylsilyl)-2-propynylidene]amino]benzenethanol with $BrZnCH_2CO_2$t-Bu in THF/NMP to produce 1,1-dimethylethyl 3S-[(2-hydroxy-1S-phenylethyl)amino]-5-(trimethylsilyl)-4-pentynoate; reacting the 1,1-dimethylethyl 3S-[(2-hydroxy-1S-phenylethyl)amino]-5-(trimethylsilyl)-4-pentynoate with sodium periodate to form 1,1-dimethylethyl 3S-[(phenylmethylene)amino]-5-(trimethylsilyl)-4-pentynoate; hydrolyzing 1,1-dimethylethyl 3S-[(phenylmethylene)amino]-5-(trimethylsilyl)-4-pentynoate to produce 1,1-dimethylethyl 3S-amino-5-(trimethylsilyl)-4-pentynoate; and transesterifying 1,1-dimethylethyl 3S-amino-5-(trimethylsilyl)-4-pentynoate and desilylating to produce ethyl 3S-amino-4-pentynoate.

The preferred chiral β-amino acid produced by the process of the present invention is useful in preparing ethyl 3S-[[4-[[4-(aminoiminomethyl)phenyl]amino]-1,4-dioxobutyl]amino]-4-pentynoate a pharmaceutical agent useful as a platelet aggregation inhibitor. Said pharmaceutical agent is more fully described in U.S. Pat. No. 5,344,957.

A preparation of ethyl 3S-amino-4-pentynoate is described in Method 3 of Scheme V of U.S. Pat. No. 5,344,957. Additional methods for preparing ethyl 3S-amino-4-pentynoate are disclosed by D. H. Hua and A. Verma, Tetrahedron Lett., 547–550 (1985) and by T. Kametani, Heterocycles, Vol. 17, 463 (1982).

U.S. Pat. No. 5,536,869 discloses a process for preparing ethyl 3S-amino-4-pentynoate monohydrochloride which comprises:

(a) treating (trimethylsilyl)acetylene sequentially with n-butyllithium and 4-formylmorpholine in the presence of an aprotic solvent followed by acid hydrolysis to give 3-(trimethylsilyl)-2-propynal;

(b) treating 3-(trimethylsilyl)-2-propynal, the product of step a, with lithium bis(trimethylsilyl)amide in the presence of an aprotic solvent to give N,3-bis(trimethylsilyl)-2-propyn-1-imine in situ, treating N,3-bis(trimethylsilyl)-2-propyn-1-imine with lithium t-butyl acetate followed by hydrolytic cleavage to give (±)1,1-dimethylethyl 3-amino-5-(trimethylsilyl)-4-pentynoate;

(c) treating (±)1,1-dimethylethyl 3-amino-5-(trimethylsilyl)-4-pentynoate, the product of step b, with p-toluenesulfonic acid in the presence of aprotic solvents to give (±)1,1-dimethylethyl 3-amino-5-(trimethylsilyl)-4-pentynoate, mono p-toluenesulfonic acid salt, treating the resulting salt with ethanol in the presence of p-toluenesulfonic acid, followed by neutralization to give (±)ethyl 3-amino-5-(trimethylsilyl)-4-pentynoate; and (d) treating (±)ethyl 3-amino-5-(trimethylsilyl)-4-pentynoate, the product of step c, with a catalytic amount of base in the presence of alkanol solvent followed by a catalytic amount of acid to give the desilylated (±)ethyl 3-amino-4-pentynoate in situ, treating (±)ethyl 3-amino-4-pentynoate with (R)-(−)-mandelic acid in the presence of aprotic solvents to give ethyl 3S-amino-4-pentynoate compounded with αR-hydroxybenzeneacetic acid; and (e) treating ethyl 3S-amino-4-pentynoate compounded with αR-hydroxybenzeneacetic acid, the product of step d, with gaseous hydrochloric acid in the presence of an aprotic solvent to give ethyl 3S-amino-4-pentynoate, monohydrochloride; with the understanding that when a pharmaceutically acceptable acid addition salt other than hydrochloride is desired the ethyl 3S-amino-4-pentynoate compounded with αR-hydroxybenzene acetic acid, the product of step d, is treated with the appropriate acid corresponding to the desired salt.

It would be desirable to provide a process for the preparation of said amino acids and preferably of ethyl 3S-amino-4-pentynoate which is amenable to scale-up, and which employs raw materials which are readily available, resulting in high yield and a high level of optical purity which doesn't require any chromatography and/or separation of diastereoisomers.

SUMMARY OF THE INVENTION

The present invention relates to a process for the preparation of chiral beta-amino acids of the formula

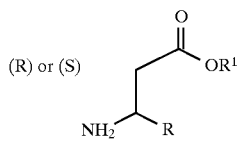

wherein R is selected from the group consisting of alkenyl, alkynyl, aryl, lower alkyl, substituted aryl, pyridyl and furanyl and $R^1$ is lower alkyl; which process comprises treating an aldehyde of the formula

with (R) or (S) phenylglycinol in tetrahydrofuran (THF) or toluene to produce an imino alcohol of the formula

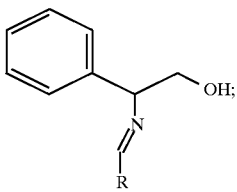

reacting said imino alcohol with $BrZnCH_2CO_2$-tBu in N-methyl pyrrolidinone (NMP), dimethylsulfoxide (DMSO) or THF followed by addition of ammonium chloride to produce an amino alcohol of the formula

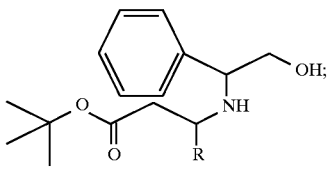

reacting the amino alcohol with sodium periodate ($NaIO_4$) or lead tetraacetate ($Pd(OAc)_4$) to form an imine of the formula

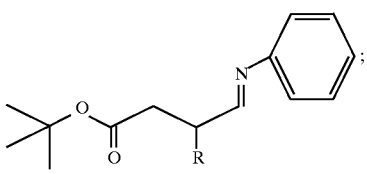

hydrolyzing said imine in the presence of para toluene sulfonic acid to produce an R or S amino acid of the formula

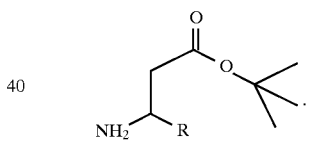

More preferably, the invention herein is directed to a process for the preparation of ethyl 3S-amino-4-pentynoate. The process involves treating 3-(trimethylsilyl)-2-propynal with L-phenylglycinol in toluene to produce αS-[[3-(trimethylsilyl)-2-propynylidene amino]benzenethanol; reacting αS-[[3-(trimethylsilyl)-2-propynylidene]amino] benzenethanol with $BrZnCH_2CO_2$t-Bu in THF/NMP to produce 1,1-dimethylethyl 3S-[(2-hydroxy-1S-phenylethyl) amino]-5-(trimethylsilyl)-4-pentynoate; reacting the 1,1-dimethylethyl 3S-[(2-hydroxy-1S-phenylethyl)amino]-5-(trimethylsilyl)-4-pentynoate with sodium periodate to form 1,1-dimethylethyl 3S-[(phenylmethylene)amino]-5-(trimethylsilyl)-4-pentynoate; hydrolyzing 1,1-dimethylethyl 3S-[(phenylmethylene)amino]-5-(trimethylsilyl)-4-pentynoate to produce 1,1-dimethylethyl 3S-amino-5-(trimethylsilyl)-4-pentynoate; and transesterifying 1,1-dimethylethyl 3S-amino-5-(trimethylsilyl)-4-pentynoate and desilylating to produce ethyl 3S-amino-4-pentynoate.

DETAILED DESCRIPTION OF THE INVENTION

The invention herein is directed to the preparation of beta-amino acids of the formula

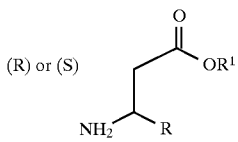

and acid addition salts thereof wherein R is selected from the group consisting of alkenyl, alkynyl, lower alkyl, aryl, substituted aryl, pyridyl, and furanyl and $R^1$ is lower alkyl.

More specifically, the invention herein is directed to the preparation of ethyl 3S-amino-4-pentynoate of the formula

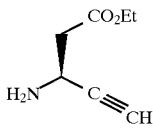

and addition salts thereof.

A synthetic scheme for the most preferred synthetic method is outlined in Scheme I and the following description thereof.

SCHEME I

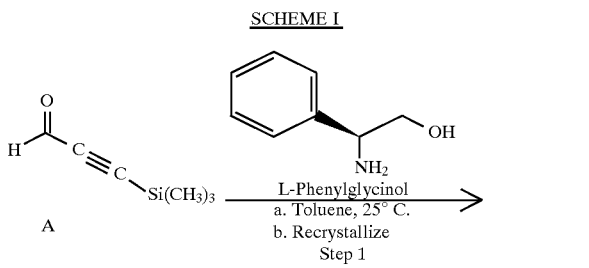

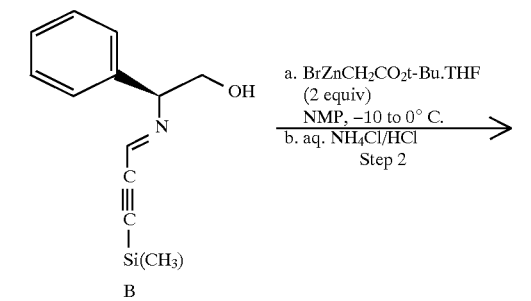

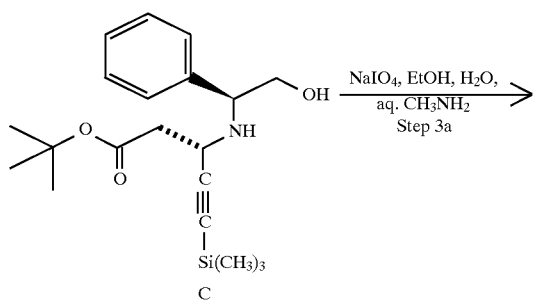

-continued
SCHEME I

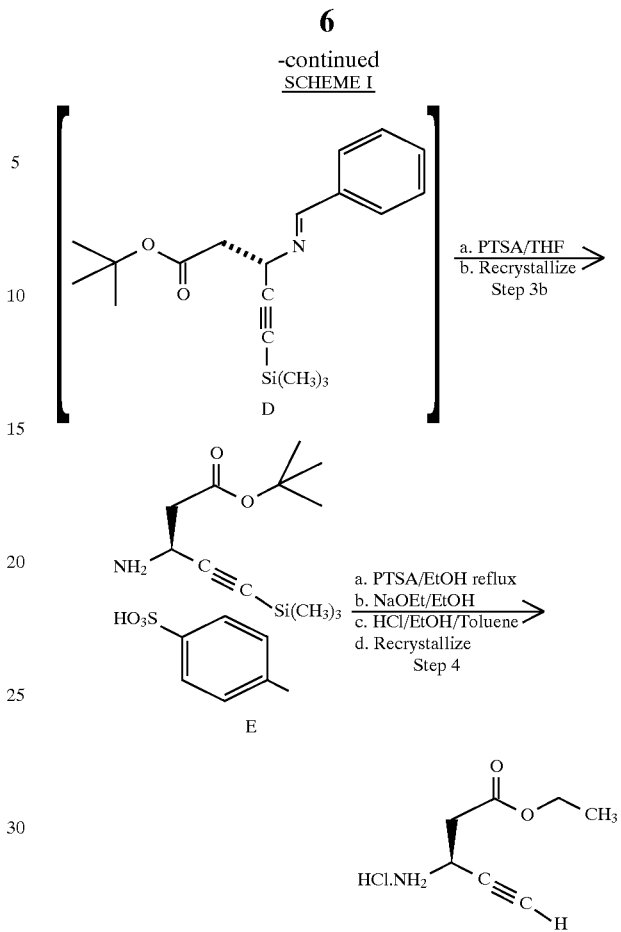

Aldehyde A is prepared according to methodology disclosed in U.S. Pat. No. 5,536,869.

In Scheme I aldehyde A is transformed to imine B by reaction with L-phenylglycinol in toluene (or alternatively in THF) followed by drying with $MgSO_4$, or molecular sieve or azeotropic distillation.

The Reformatsky reagent $BrZnCH_2CO_2t$-Bu is prepared in THF by fast activation of zinc with dibromoethane (2–5 mole %) (alternatively, zinc is activated with diluted HCl followed by drying with THF and high vacuum or with tetramethylsilane (1–5%) in THF at 25° C.), followed by reaction with tert-butyl bromoacetate at 50° C. A solution of $BrZnCH_2CO_2t$-Bu is prepared by removing the THF by distillation, followed by dissolution in NMP or DMSO or by filtration of the solid reagent followed by dilution with an aprotic solvent such as NMP or DMSO.

A solution of imine B in NMP (or alternatively in DMSO or THF) is added to a solution of the Reformatsky reagent in an aprotic polar solvent such as THF, NMP, NMP/THF or DMSO, followed by quenching with aqueous ammonium chloride and aqueous hydrochloric acid and subsequent extraction with methyl tert-butyl ether (MTBE) or EtOAc. The organic solution is washed with aqueous ammonium chloride, water and brine to give the amino alcohol C.

The amino alcohol C is reacted with $NaIO_4$ in the presence of aqueous methylamine in ethanol/water followed by filtration, dilution with toluene, MTBE or THF to give a solution of imine D. [Alternatively, the reaction mixture can be concentrated and extracted with MTBE, filtered, dried, filtered and concentrated.]

Imine D is hydrolyzed in the presence of para-toluenesulfonic acid in MTBE (or alternatively in THF or toluene). Precipitation with heptane and filtration afforded the para-toluenesulfonic acid salt E.

Transformation of para-toluenesulfonic acid salt E to hydrochloride salt F is achieved by successive reaction with 0.3 equivalents para-toluenesulfonic acid in ethanol, followed by basic work up (aqueous solution of sodium bicarbonate or potassium bicarbonate) and extraction, with sodium ethoxide in ethanol, with HCl in EtOH (generated by the addition of acetyl chloride in EtOH or dissolution of HCl gas in ethanol) and recrystallization in acetonitrile/MTBE (or alternatively acetonitrile/toluene or acetonitrile/heptane).

SCHEME II

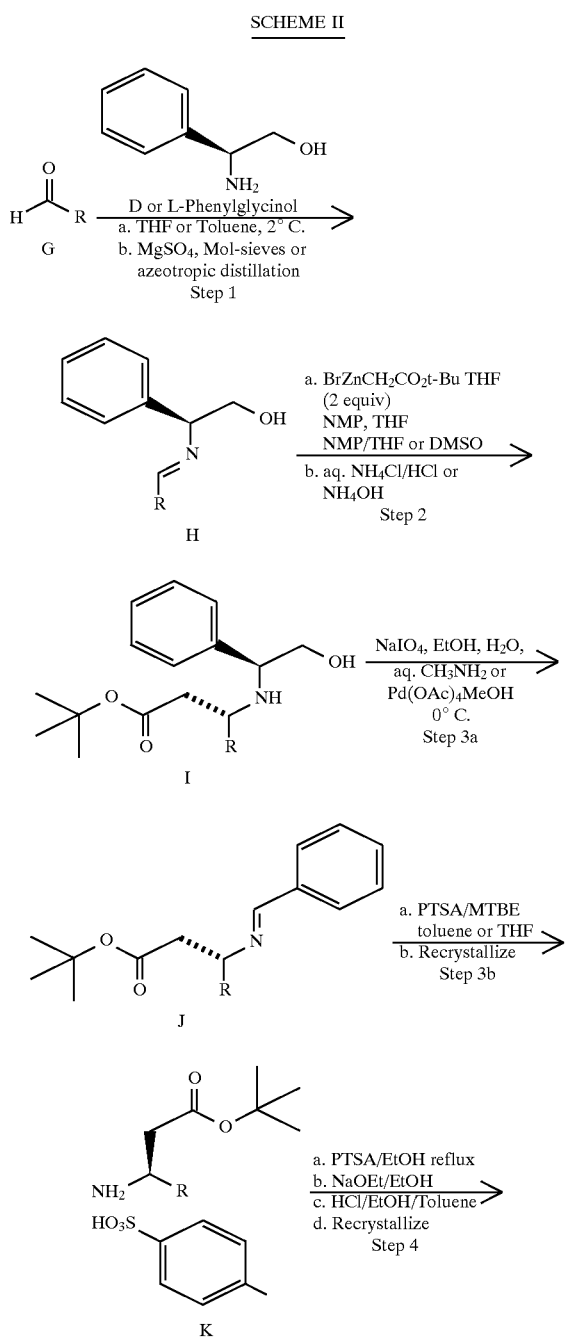

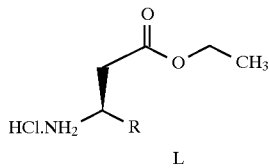

L

In Scheme II aldehyde G (R=alkynyl, alkyl, aryl, substituted aryl, pyridinyl, furanyl) is transformed to imine H by reaction with D or L phenylglycinol in THF or toluene, followed by drying with MgSO$_4$, molecular sieves or by azeotropic distillation.

The Reformatsky reagent BrZnCH$_2$CO$_2$t-Bu is prepared in THF by fast activation of zinc with dibromoethane (1–5 mole %) (alternatively, the zinc is activated with diluted HCl followed by drying with THF and high vacuum or tetramethylsilane (TMS) in THF at 25° C.), followed by reaction with tert-butyl bromoacetate at 50° C. A solution of the reagent is prepared by removing the THF by distillation or decantation followed by dissolution in an aprotic polar solvent such as NMP or DMSO or by filtration of the solid reagent followed by dilution with an aprotic polar solvent such as NMP or DMSO.

A solution of imine H in an aprotic polar solvent such as NMP, DMSO or THF, is added to a solution of the Reformatsky reagent in an aprotic polar solvent such as NMP, NMP/THF, DMSO or THF, followed by acidic aqueous (ammonium chloride/HCl) or basic (ammonium hydroxide) quench and subsequent extraction with MTBE or EtOAc, washing with aqueous ammonium chloride, water and brine to produce the amino alcohol I.

The amino alcohol I is reacted with NaIO$_4$ in the presence of methylamine in ethanol/water or lead tetraacetate in methanol followed by filtration, dilution with toluene, MTBE or THF to give a solution of imine J. Alternatively, the reaction mixture can be concentrated and extracted with MTBE, filtered, dried, filtered and concentrated.

Imine J is hydrolyzed in the presence of para-toluenesulfonic acid in THF, toluene or MTBE. Precipitation with heptane and filtration afforded the para-toluenesulfonic acid salt K with configuration D (from D-phenylglycinol) or L (from L-phenylglycinol).

Transformation of para-toluenesulfonic acid salt K (R=2-trimethylsilyl-ethynyl) to hydrochloride salt L (R=ethynyl) is achieved by successive reaction with para-toluenesulfonic acid in a solvent such as ethanol, followed by basic work up (aqueous solution of sodium bicarbonate or potassium bicarbonate) and extraction, with sodium ethoxide in an alkanol such as ethanol, with HCl in EtOH (generated by addition of acetyl chloride in an alkanol solvent such as ethanol or dissolution of HCl gas in ethanol) and recrystallization in acetonitrile/MTBE (or alternatively acetonitrile/toluene or acetonitrile/heptane).

Unless otherwise noted the starting materials for the process of this invention are all commercially available or can be prepared according to conventional methods known to those with skill in the art. All equipment employed is commercially available.

The following is a list of definitions and abbreviations used herein:

The terms "alkyl" or "lower alkyl" refer to straight chain or branched chain hydrocarbon radicals having from about 1 to about 6 carbon atoms. Examples of such alkyl radicals include methyl, ethyl, n-propyl, isopropyl, n-butyl, isobutyl, sec-butyl, t-butyl, pentyl, hexyl and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry. Examples of such groups are ethenyl, propenyl, butenyl, isobutenyl, pentenyl, hexenyl and the like.

As used herein the terms "alkynyl" and "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "aryl" as used herein denotes aromatic ring systems composed of one or more aromatic rings, preferably consisting of one or two aromatic rings. The term embraces aromatic radicals such as phenyl, naphthyl, triphenyl, benzofuran and the like.

The term "substituted aryl" as used herein denotes an aryl radical as defined above substituted by one or more substituent selected from the group consisting of alkyl, amino, hydroxy, chloro, fluoro, bromo, alkoxy and nitro.

The terms "pyridyl" or "pyridinyl" are represented by a radical of the formula

The term "furanyl" is represented by a radical of the formula

The term "L-phenylglycinol" refers to a radical of the formula and is used interchangeably with the term (S)-phenylglycinol.

The term "D-phenylglycinol" refers to a radical of the formula and is used interchangeably with the term (R)-phenylglycinol.

THF refers to tetrahydrofuran.
NMP refers to N-methylpyrrolidinone.
DMSO refers to dimethylsulfoxide.
NaIO$_4$ refers to sodium periodate.
NH$_4$Cl refers to ammonium chloride.
CH$_3$NH$_2$ refers to methylamine.
EtOH refers to ethanol.
Pb(OAc)$_4$ refers to lead tetraacetate.
PTSA refers to para-toluenesulfonic acid.
MTBE refers to methyl tert-butyl ether.
NaOEt refers to sodium ethoxide.
EtOAc refers to ethyl acetate.
MgSO$_4$ refers to magnesium sulfate.
GC refers to gas chromatography.

The present invention provides a safe, convenient and cost effective manufacturing process for the preparation of ethyl 3S-amino-4-pentynoate which is amenable to scale-up. The process utilizes raw materials which are readily available and cost efficient. Its convenience is demonstrated in that the synthetic route does not require either a chromatography or chemical or enzymatic separation of diastereoisomers. Its cost effectiveness is demonstrated by the final products being produced in high yield and a high level of optical purity.

The following non-limiting examples describe and illustrate a method for carrying out the process of the present invention, as well as other aspects of the invention, and the results achieved thereby in further detail. Both an explanation of, and the actual procedures for, the various aspects of the present invention are described where appropriate. These examples are intended to be illustrative of the present invention, and not limiting thereof in either scope or spirit. Those of skill in the art will readily understand that known variations of the conditions and processes described in these examples can be used to perform the process of the present invention.

EXAMPLE 1

αS-[[3-(trimethylsilyl)-2-propynylidene]amino]benzenethanol

To a slurry of L-phenylglycinol in toluene (10.00 g, 72.9 mmoles/55 ml), at ambient temperature, was added 1.05 equivalent of 3-(trimethylsilyl)-2-propynal (9.66 g, 76.5 mmoles) at such rate as to keep the temperature below 30° C. The mixture was stirred at ambient temperature for 1 hour. The water was azeotropically removed with toluene under reduced pressure to a final weight of 28.2 g (1.5×the expected yield). At room temperature and with stirring 75 ml of heptane was added and the mixture was cooled to −10° C. for 8 hours. Filtration of the solids by suction followed by a heptane rinse of the cake and air drying produced the solid imine αS-[[3-(trimethylsilyl)-2-propynylidene]amino] benzenethanol (80%:15.00 g) in 4:1 ratio of anti to syn isomers (as determined by NMR in THF).

mp 78°–80° C.; $^1$HNMR (THF-d8) anti-isomer, δ0.20 (s, 9H) 3.61 (t, 1H, J=6.3 Hz), 3.95 (t, 1H, J=6.3 Hz), 4.18 (t, 1H, J=6.3 Hz), 7.17 (tt, 1H, J=7.3, 1.4 Hz), 7.25 (complex t, 2H, J=7.3 Hz), 7.35 (complex d, 2H, J=7.3 Hz), 7.57 (s, 1H). Syn-isomer, δ0.22 (s, 9H), 3.76–3.63 (complex band, 3H), 5.01 (m, 1H), 7.16 (tt, 1H, 7.3, 1.4 Hz), 7.23 (complex t, 2H, J=7.3 Hz), 7.33 (complex d, 2H, J=7.3 Hz), 7.56 (d, 1H); $^{13}$C NMR (THF-d8) anti-isomer, δ–0.3, 67.9, 79.3, 96.5, 103.5, 127.9, 128.2, 129.0, 141.9, 145.4. Syn-isomer, δ–0.4, 68.6, 73.2, 98.2, 103.6, 127.7, 128.6, 128.9, 142.4, 143.3; IR (MIR) ν (cm-1) 1610, 2370, 2340, 3390, 3610 cm$^{-1}$.

Analysis Calculated for $C_{14}H_{19}NOSi$: C, 68.52; H, 7.80; N, 5.71. Found: C, 68.59; H, 7.52; N, 5.71.

EXAMPLE 2

$BrZnCH_2CO_2t\text{-}Bu$

Step A

A 4 liter jacketed flask, fitted with a condenser, temperature probe and mechanical stirrer was charged with 180 g of Zn metal (–30–100 mesh, 180.0 g, 2.77 mole) and 1.25 L of THF was added to the vessel. While stirring, 1,2-dibromoethane (4.74 mL, 0.055 mole) was added to the vessel via a syringe. The suspension of zinc in THF was heated to reflux (65° C.) and maintained at this temperature for 1 hour. The mixture was cooled to 50° C. before charging the tert-butyl bromoacetate (488 g, 369 mL, 2.5 moles) over a 1.5 hour time period. Controlled reagent addition was performed with a 50 ml syringe and syringe pump (addition rate set at 4.1 mL/min). A temperature of 50° C.±5° C. was maintained during the addition. The reaction mixture was allowed to stir at 50 ° C. for 1 hour after the addition was complete. The reaction mixture was allowed to cool to 25° C., and the agitation turned off to allow the precipitate to settle (the product precipitates from THF solution at 31° C.). The THF mother liquor was removed by decantation into a 2 L round bottom flask under partial vacuum (20 mm Hg) with a dip tube (coarse fritted glass filter). This removed 65% of THF from the vessel, 800 mL of NMP was added and agitation resumed for 5 minutes at 25° C. The reaction mixture was transferred to another vessel by filtration to remove the remaining zinc. Alternatively, the solid reagent can be filtered and dried under $N_2$ using a pressure funnel. The cake is washed with THF and a white solid was obtained. The solid was dried for 1–2 hours. Typical recovery is 85–90%. The solid can be stored at –20° C. (for at least 6 months).

Step B

Titration Method.

A 1.0 mL aliquot of the Reformatsky-NMP/THF solution was removed from the reaction mixture via syringe and added to a 25 mL round bottom flask which contained a pre-weighed amount of benzaldehyde (250–300 mg) and a magnetic stir bar, under a nitrogen atmosphere. The reaction mixture was stirred for 30 minutes at room temperature. To the flask was added 5.0 mL of aqueous 29% $NH_4Cl$ and 5.0 mL of methyl t-butyl ether (MTBE). The resulting mixture was stirred for 5 minutes at room temperature. The agitation was stopped and the layers allowed to separate over 5 minutes. A 1.0 mL aliquot of the organic layer was removed and diluted to 25 mL with MTBE in a volumetric flask. This solution was analyzed by gas chromatography (GC) to determine the amount of benzaldehyde which remained. Standard solutions of benzaldehyde in MTBE at concentrations of 0.04M, 0.01M, and 0.002M were co-injected with the sample. The sample concentration was determined from the linearity plot of the standard solutions and the sample GC peak area. The concentration of the Reformatsky solution was determined using the following calculation:

Amount of remaining benzaldehyde=concentration of sample (g/L)*50*5/2

Titer (Mole/L)=Pre-weighted amount of benzaldehyde—amount remaining/106

Yield=Mole/liter*Total volume of solution/Theoretical 100% yield.

Analytical determination of the titer was 1.57 molar with a molar yield of 94% of Example 2.

EXAMPLE 3

1,1-dimethylethyl 3S-[(2-hydroxy-1S-phenylethyl) amino]-5-(trimethylsilyl)-4-pentynoate

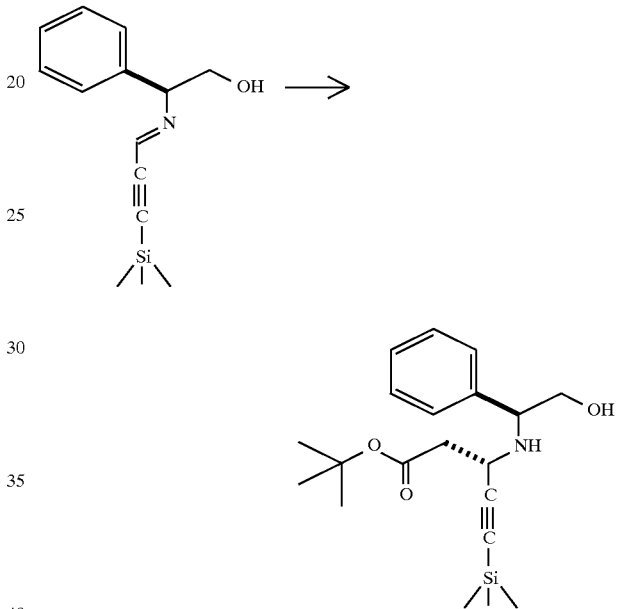

A solution of the product of Example 2 in NMP/THF (2.6/1, 1.5 L, 1.57M, 2.4 moles) was charged in a 4 L flask (jacketed, 4 ports fitted with mechanical stirrer, teflon coated temperature probe and addition funnel). The solution was cooled to –10° C. and a solution of the imine of Example 1 (220.0 g, 0.96 mole) in NMP (0.250 L) was added after 30 minutes while the temperature was maintained at –3° C. After total conversion (less than 1% of starting material), as determined by gas chromatography (GC), a mixture of 29% ammonium chloride aqueous solution (1.0 L) and 2N HCl (0.5 L) was added in 15 minutes from –10° C. to 13° C. The mixture was warmed to 25° C. and MTBE (1.0 L) was added. The mixture was stirred for 30 minutes and the layers were separated. The aqueous layer was extracted with MTBE (0.5 L). The organic layers were combined and washed successively with a 29% solution of $NH_4Cl$ (0.5 L), $H_2O$ (0.5 L) and brine (0.5 L) and were concentrated under reduced pressure to afford an orange oil (366 g) containing the title compound (84 wt %, 91% yield determined by GC quantitation) 1,1-dimethylethyl 3R-[(2-hydroxy-1S-phenylethyl)amino]-5-(trimethylsilyl)-4-pentynoate, (mixture obtained with a diastereomeric excess (de) of 80% as determined by chiral HPLC).

The two isomers were separated by preparative chiral HPLC for analytical purpose:

Data for 1,1-dimethylethyl 3R-[(2-hydroxy-1S-phenylethyl)amino]-5-(trimethylsilyl)-4-pentynoate: $^1$H NMR (CDCl$_3$, TMS) δ(ppm) 0.16 (s, 9H); 1.45 (s, 9H), 2.52 (dd (AB), 1H, J=5.6, 15.3 Hz), 2.56 (dd, (AB), 1H, J=5.6, 15.3 Hz), 3.55 (dd, 1H, J=7.7, 5.6 Hz), 3.59 (dd, 1H, J=8.5, 10.7 Hz), 3.74 (dd, 1H, J=4.5, 10.8 Hz), 4.15 (dd, 1H, J=4.5, 8.4 Hz), 7.27 to 7.34 (m, 5H); $^{13}$C NMR (CDCl$_3$) δ(ppm): 0.05, 28.08, 42.22, 44.86, 67.21, 67.47, 80.95, 88.61, 105.00, 127.74, 128.52, 139.69, 170.06; DSC: 79.68° C. (endo. 71.68 J/g), 237.33° C. (exo. 169.0 J/g); $[α]^D_{25}$=+179.3° (c=0.36, CHCl$_3$); IR (MIR) ν (cm-1) 2167, 1735; UV (methanol) λmax (nm)=204 (abs=0.37); Microanalytical: calcd for C$_{20}$H$_{31}$NO$_3$Si: C, 66.44; H, 8.64; N, 3.87. Found: C, 66.34; H, 8.88; N, 3.89.

Data for 1,1-dimethylsilyl 3S-[(2-hydroxy-1S-phenylethyl)amino]-5-(trimethylethyl)-4-pentynoate: $^1$H NMR (CDCl$_3$, TMS) δ(ppm) 0.09 (s, 9H); 1.46 (s, 9H), 2.49 (dd (AB), 1H, J=8.6, 15.6 Hz), 2.59 (dd, (AB), 1H, J=5.1, 15.6 Hz), 3.59 (dd, 1H, J=6.5, 11.1 Hz), 3.77 (dd, 1H, J=4.5, 11.1 Hz), 3.89 (dd, 1H, J=5.1, 8.7 Hz), 3.97 (dd, 1H, J=5.1, 8.7 Hz), 7.24 to 7.36 (m, 5H); $^{13}$C NMR (CDCl$_3$) δ(ppm): −0.11, 28.07, 42.26, 46.15, 62.10, 65.48, 81.16, 88.28, 105.99, 127.33; DSC: 252.27° C. (exo. 342.3 J/g); $[α]^D_{25}$=−5.6° (c=1.024, CHCl$_3$); IR (neat) ν (cm−1) 2167, 1735; UV (methanol) λmax (nm)=205 (abs=0.33);

Microanalytical: calcd for C$_{20}$H$_{31}$NO$_3$Si: C, 66.44; H, 8.64; N, 3.87. Found: C, 66.22; H, 8.82; N, 3.85.

EXAMPLE 4

1,1-dimethylethyl 3S-[(phenylmethylene)amino]-5-trimethylsilyl)-4-pentynoate

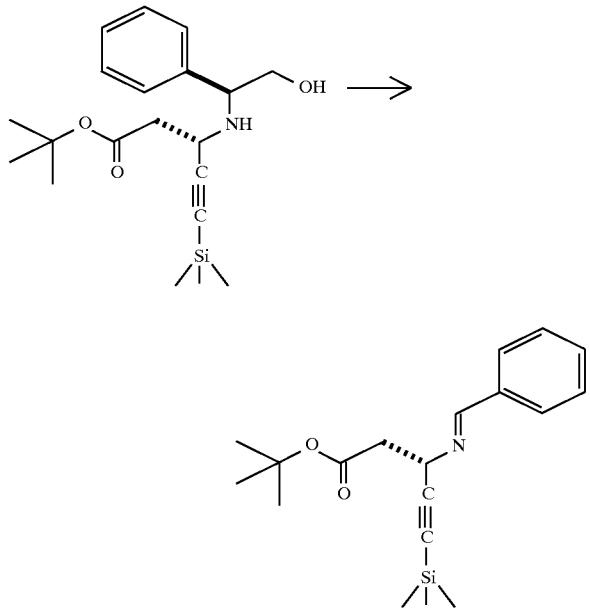

NaIO$_4$ (77.0 g, 0.36 mole) was charged into a flask (500 mL) followed by H$_2$O (0.330 L) and the mixture was stirred for 30 minutes at 25° C. A solution of 1,1-dimethylethyl 3S-[(2-hydroxy-1S-phenylethyl)-amino]-5-(trimethylethyl)-4-pentynoate of Example 3 (116.3 g, 86 wt %, 0.277 mole) in ethanol (0.520 L) was charged into a 1 L flask (4 ports, jacketed, fitted with mechanical stirrer and teflon coated temperature probe) purged with N$_2$, followed by addition of a solution of methylamine (40 wt %, 24 mL, 0.278 mole).

After 5 minutes of stirring at 25° C., a slurry of NaIO$_4$ in H$_2$O was added portionwise while maintaining a temperature below 35° C. (32°±2° C.). After complete addition, conversion was complete and the mixture was cooled to 3° C. and held at this temperature for 3 hours. The mixture was filtered on a pressure filter (extra coarse, 600 mL) and the cake was dried for 3.5 hours under a N$_2$ vacuum (Karl-Fisher analysis showed 5.60% H$_2$O remaining). The cake containing a mixture of the title compound and iodate salt was charged into a flask (500 mL) and toluene (130 mL) was added. After 30 minutes of stirring at 30° C. the mixture was filtered. The cake was washed twice with toluene (2×50 mL). The 3 fractions were combined and partially concentrated to a weight of 161 g containing 53.3 wt % of the title compound (determined by GC quantitation) with a yield of 92% and a chiral purity of 99.9% (determined by chiral HPLC). A sample was isolated for full characterization by concentration of the solution:

$^1$H NMR (CDCl$_3$, TMS) δ(ppm) 0.20 (s, 9H); 1.45 (s, 9H), 2.66 (dd (AB), 1H, J=7.0, 15.0 Hz), 2.80 (dd, (AB), J=7.7, 15.0 Hz), 4.83 (dt, 1H, J=1.7, 7.6 Hz), 7.38 to 7.44 (m, 3H), 7.74 to 7.77 (m, 2H), 8.56 (d, 1H, J=1.5 Hz); $^{13}$C NMR (CDCl$_3$) δ(ppm): 0.02, 28.09, 43.20, 56.46, 80.75, 92.53, 103.15, 128.47, 128.54, 130.90; 135.90, 161.78, 169.55; DSC: 72.22° C. (endo. 112.4 J/g); $[α]^D_{25}$=−35.5° (c=1.16, CHCl$_3$); IR (MIR) ν (cm−1) 2174, 1728, 1641; UV (methanol) λmax (nm)=205 (abs=1.004), 248 (abs=0.655); Microanalytical: calcd for C$_{19}$H$_{27}$NO$_2$Si: C, 69.26; H, 8.26; N, 4.25. Found: C, 69.10; H, 8.43; N, 4.33.

EXAMPLE 5

1,1-Dimethylethyl 3S-amino-5-(trimethylsilyl)-4-pentynoate 4-methylphenylsulfonate salt

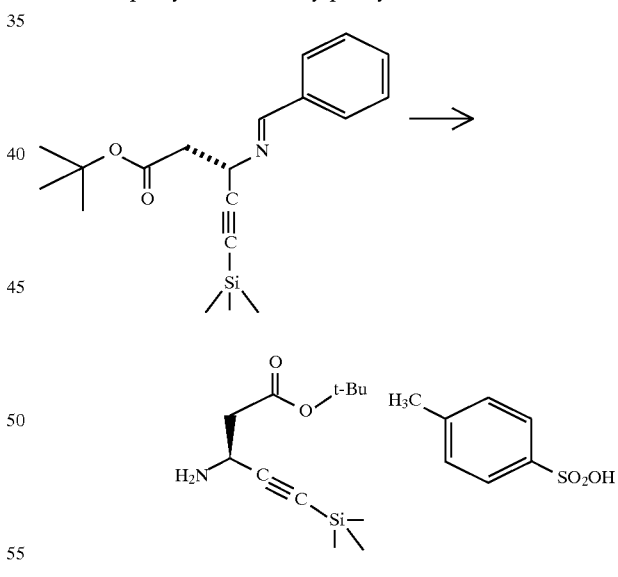

A solution of the product of Example 4 (123.3 g, 0.374 mole) in dry THF (350 mL) was prepared. p-Toluenesulfonic acid monohydrate (71.2 g, 0.374 mole) was charged to a 4 L jacketed reaction vessel under nitrogen. An overhead stirrer with a 10 cm teflon stir blade was attached. A thermocouple thermometer was put in place. The reactor jacket was cooled to 0° C. The solution of the product of Example 4 was added via an addition funnel over 5 minutes with stirring at 250 rpm. The reaction temperature rose to 10° C. The addition funnel was rinsed with THF (300 mL). After stirring for 15 minutes the mixture became homogeneous. The stirring rate was increased to 350 rpm. Skellysolve C heptanes (1360 mL) was added over 5 minutes. The product crystallized and the agitation was increased to 540 rpm. The solvent was distilled from the reactor under vacuum under the following conditions. An oil pump connected to a vacuum regulator which was used to adjust the vacuum to 45 mm Hg. The jacket temperature was set to 20° C. and a dry ice/isopropanol condenser with 2 L receiving flask was used to collect the distillate. The distillate collected was 900 mL. The reactor was placed under a nitrogen atmosphere and further heptanes (900 mL) were added. The slurry was cooled to 2° C. The solids were collected on a 10 cm coarse glass fritted filter using vacuum. The reaction vessel was rinsed by adding heptanes (500 mL) and THF (50 mL) with stirring. The reaction mixture was cooled to 10° C. and added to the filter. The cake was washed with heptanes (3×300 mL) and dried by using a combination of vacuum and nitrogen flow for 4.5 hours to produce the title compound (145.9 g, 94%): mp. 142° C.;

$^1$H NMR (CDCl$_3$, 400 MHz) δ8.32 (br, s, 3H), 7.79 (d, J=8.0 Hz, 2H), 7.15 (d, J=8.0 Hz, 2H), 4.40 (dd, J=8.0, 6.0 Hz, 1H), 2.89 (dd, J=17.0, 8.0 Hz, 1H), 2.76 (dd, J=17.0, 5.0 Hz, 1H), 2.36 (s, 3H), 1.41 (s, 9H), 0.10 (s, 9H); $^{13}$C NMR (CDCl$_3$, 125 MHz) δ168.60, 141.55, 140.22, 128.81 (2C), 126.11 (2C), 98.51, 92.71, 82.02, 40.56, 38.56, 27.95 (3C), 21.31, −0.53 (3C); Analysis Calculated for C$_{19}$H$_{31}$NO$_5$SSi: C, 55.17; H, 7.55; N, 3.39. Found: C, 55.27; H, 7.27; N, 3.34.

EXAMPLE 6 ethyl 3S-amino-4-pentynoate, monohydrochloride salt

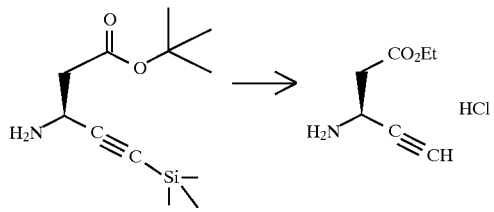

A solution of the product of Example 5 (500.0 g, 1.21 mol) and p-toluenesulfonic acid monohydrate (69.5 g, 0.365 mol) in ethanol (930 mL) was heated to reflux and held for 4 hours. Reaction completion was determined by GC. The reaction mixture was concentrated in vacuo. MTBE (1200 mL) was charged to the concentrate with stirring to afford complete dissolution. A 20 wt/wt % potassium bicarbonate aqueous solution (1387 g) was added to the MTBE solution. The biphasic mixture was stirred for 15 minutes. The aqueous layer was back-extracted with MTBE (700 mL). The combined organic layers were extracted a second time with a 20 wt/wt % potassium bicarbonate aqueous solution (306 g). The organic layer was concentrated in vacuo. Water was removed azeotropically with ethanol (900 mL) under reduced vacuum. An 87% yield of the desired silyl protected free amine was obtained [1.06 mol]. To the concentrate was charged ethanol 2B (600 mL), followed by 21 wt % sodium ethoxide (in ethanol denatured with 5% toluene) (39.6 mL, 0.106 mol, 0.1 equivalent sodium ethoxide). The reaction solution was allowed to cool to room temperature and stirred for one-half hour. Desilylation completion was determined by GC. In a separate vessel was charged ethanol 2B (720 mL), followed by acetyl chloride (81.6 mL, 1.15 mol, 1.1 equivalent). This addition was carried out over 20 minutes, not allowing the temperature to rise above 45° C. The solution was then cooled to 20°–25° C. The resulting hydrogen chloride/ethyl acetate/ethanol solution was charged to the desilylation reaction mixture. The reaction mixture was cooled to 25° C. with stirring over a 30 minute period and then stirred at 25° C. for an additional 30 minutes. The reaction mixture was concentrated under reduced pressure. The concentrate was cooled to room temperature and toluene (920 mL) was added. The mixture was stirred for 20 minutes and then concentrated in vacuo. Toluene (920 mL) was added to the concentrate and stirred for 20 minutes. Solids were collected by filtration and dried affording 184.94 g of crude title compound (86.1% yield).

A portion of the crude title compound (80.0 g) was recrystallized from acetonitrile/MTBE. To 80.0 g of crude title compound was added 400 mL acetonitrile. The mixture was heated to reflux and the resulting heated opaque yellow solution was filtered through 20 g celite which had been washed with 160 mL hot acetonitrile. The filtrate was concentrated in vacuo removing 195 mL of solvent. The concentrated solution was cooled to 45° C. To the solution was added 195 mL of MTBE. The resulting opaque mixture was heated to reflux, cooled to 50° C. and stirred for 15 minutes. The mixture was cooled to 40° C. and held for 15 minutes. The mixture was then allowed to cool to 22° C. and filtered. The resulting solids were rinsed with 2×80 mL MTBE. The solids were dried on the filter for 10 minutes, then under high vacuum for 2 hours, providing 72.18 g of the title compound.

$^1$H NMR (D$_6$-DMSO) δ(ppm) 1.21 (t, 3H, J=7 Hz), 2.84 (dd, 1H, J=9, 16 Hz), 3.03 (dd, 1H, J=5, 16 Hz), 3.70 (d, 1H, J=2Hz), 4.13 (q, 2H, J=7 Hz), 4.31 (m, 1H), 8.82 (s, 3H); $^{13}$C NMR (D$_6$-DMSO) δ(ppm): 13.95, 37.58, 38.40, 60.71, 77.99, 78.63, 168.42; DSC: 125°–131° C. (endo. 107.2 J/g); $[α]^D_{25}$ =−6.7; IR (MIR) ν (cm$^{-1}$) 3252, 2128, 1726;

Microanalytical: calcd for C$_7$H$_{12}$NO$_2$Cl: C, 47.33; H, 6.81; N, 7.89; Cl, 19.96: Found: C, 47.15; H, 6.84; N, 7.99; Cl, 19.55.

SCHEME II

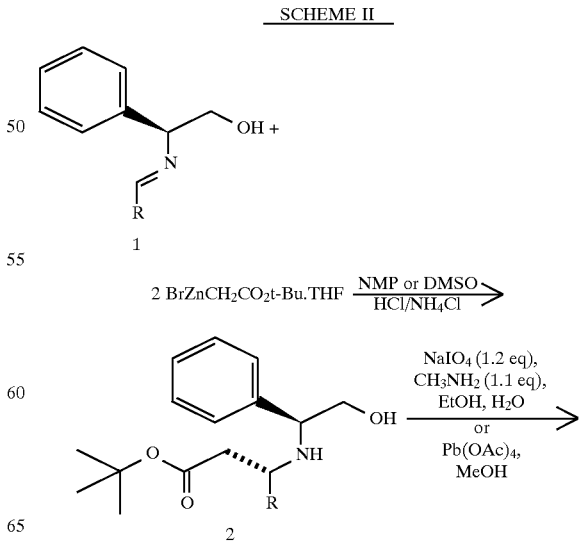

-continued
SCHEME II

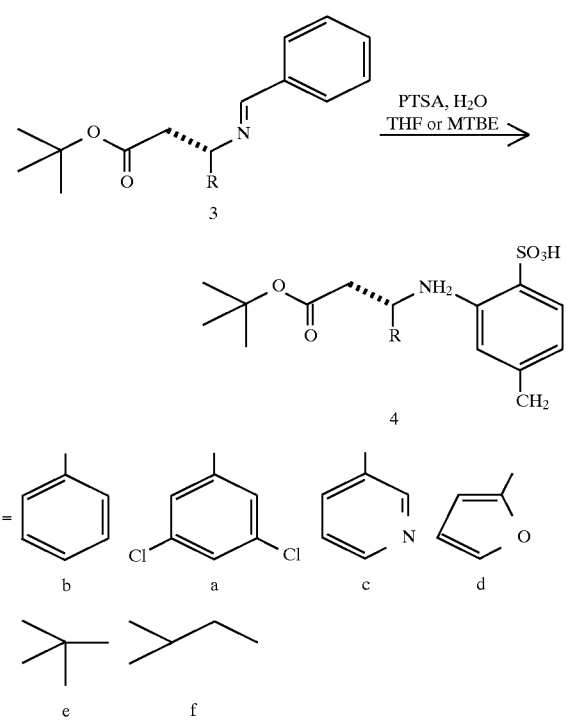

Scheme III depicts the preparation of other β-amino esters using the process of the present invention as described hereinafter.

EXAMPLE 7

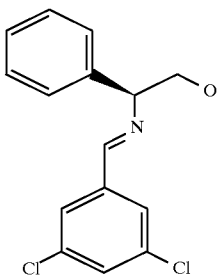

(S)-Phenyl glycinol (11.74 g, 0.086 mole) was charged in a 500 mL 3N RB flask fitted with a mechanical stirrer, followed by addition of toluene (110 ml). The flask was vacuum/flushed with nitrogen. 3,5-dichlorobenzaldehyde (15.0 g, 0.086 mole) was added. After 15 minutes at 22° C., MgSO$_4$ (15 g) was added (exothermic reaction). The mixture was stirred for 1 hour at 22° C., filtered on a coarse fritted filter. The cake was washed with toluene (20 ml). The solutions were combined and concentrated under reduced pressure to afford 27.00 g of a pale yellow oil containing the imine 1a. No further purification was performed and the crude product was used directly in the coupling reaction. $^1$H NMR (CDCl$_3$), TMS) mixture of imine and oxazoline 4/1. (ppm):(imine) 3.88 to 3.99 (m, 2H), 4.50 (dd, 1H, J=4.7, 8.1 Hz) 7.67 (d, 2H), 8.28 (s, 1H):oxazoline: 5.55 and 5.70 (s, 0.5+0.5H), 3.72 to 3.83 (m, 0.5+0.5 H), 4.30 to 4.35 (m, 0.5+0.5H), 4.40 to 4.48 (m, 0.5H), 4.54 to 4.60 (m, 0.5H), mixed protons: 7.15 to 7.47 (m(aromatic+CDCl$_3$)); $^{13}$C NMR (CDCl$_3$, TMS) (ppm):imine: 67.55, 76.38, 135.13, 138.70, 140.05, 159.72. Oxazoline: 60.60, 62.80, 72.12, 72.34, 91.05, 91.68, 135.03, 135.41, 142.62. Mixed signals: (aromatics) 124.86, 124.956, 125.33, 126.53, 126.65, 126.75, 127.38, 127.74, 127.77, 128.11, 128.26, 128.32, 128.72, 128.84, 128.93, 129.06, 130.64.

EXAMPLE 8

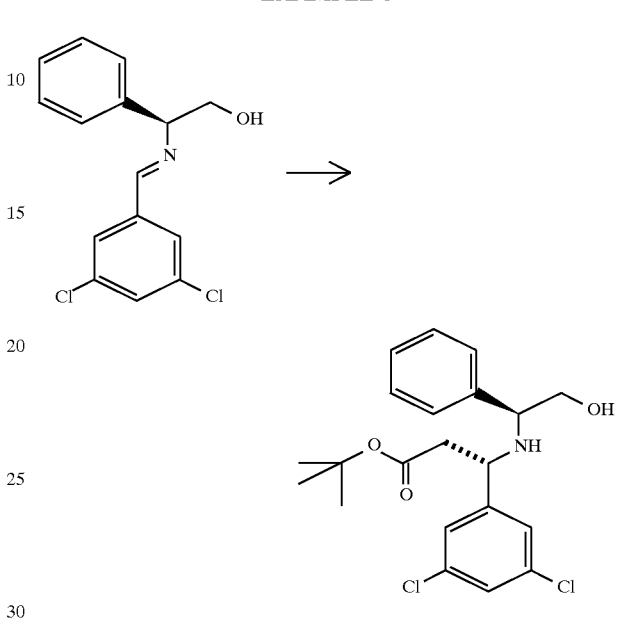

A1 L jacketted 3 ports reactor with bottom valve, fitted with a mechanical stirrer and an addition funnel was charged with a solution of Reformatsky reagent from Example 2 (189 mmoles, 165 ml, 1.15M). The solution was then cooled to −10° C. A solution of imine from Example 7 (25.39 g, 85.8 mmoles) in NMP (60 ml) was prepared under nitrogen and charged in the addition funnel. The solution of imine was then added in 5 minutes while the temperature was maintained at −5° C. (jacket at −10° C.). The reaction was monitored by GC and TLC (elution heptane/EtOAc 30%). After 5 minutes the reaction was almost complete (trace of starting material). The mixture was stirred for an additional hour and a mixture of 2N HCl/saturated solution of NH$_4$Cl (½, 135 ml) was added. MTBE (200 ml) was added and the mixture was stirred for 1 hour at 23° C. Stirring was stopped and the layers were separated. The aqueous layer was extracted with MTBE (100 ml). The two organic layers were combined, washed successively with a saturated solution of N$_4$Cl (140 ml), water (140 ml) and brine (140 ml). The solution was dried with MgSO$_4$ (30 g), filtered and concentrated to afford 35.2 g of an orange oil containing the desired product 2a as a single diastereoisomer (by $^1$H NMR).

In a separate reaction (28.6 mmole scale) the crude product (11.36 g) was purified by chromatography (SiO2, 200 g), elution heptane/EtOAc 30%) to afford the desired compound 2a as a pale yellow oil (10.07 g, 85%). $^1$H NMR (CDCl$_3$, TMS) δ(ppm) 1.40 (s, 9H), 2.56 (dd (AB), 1H, J=5.6, 15.4 Hz), 2.56 (dd (AB), 1H, J=8.1, 15.6 Hz), 2.60 (s(broad), 1H), 3.62 (dd (AB), 1H, J 6.8, 10.7 Hz), 3.72 (dd, 1H, J=4.2, 6.8 Hz), 3.80 (dd (AB), 1H, J=4.2, 6.8 Hz), 4.11 (dd, 1H, J=5.8, 7.9 Hz), 7.09 to 7.29 (m, 8H, (aromatic)); $^{13}$C NMR (CDCl$_3$, TMS) δ(ppm):28.00, 42.98, 57.28, 62.24, 65.99, 81.42, 125.69, 127.21, 127.35, 127.60, 128.48, 134.83, 140.78, 146.44, 170.58; DSC: 241.46° C. (endo. 180.1 J/g); [α]$^D_{25}$=+6.9° (c=1.025, CHCl$_3$); IR (MIR) (cm−1) 1726, 1587, 1567.

Microanalytical: calcd for $C_{21}H_{25}Cl_2NO_3$: C: 61.47; H: 6.14; N: 3.41; Cl: 17.27 Found: C: 59.95; H: 6.51; N: 3.11; Cl: 16.00

EXAMPLE 9

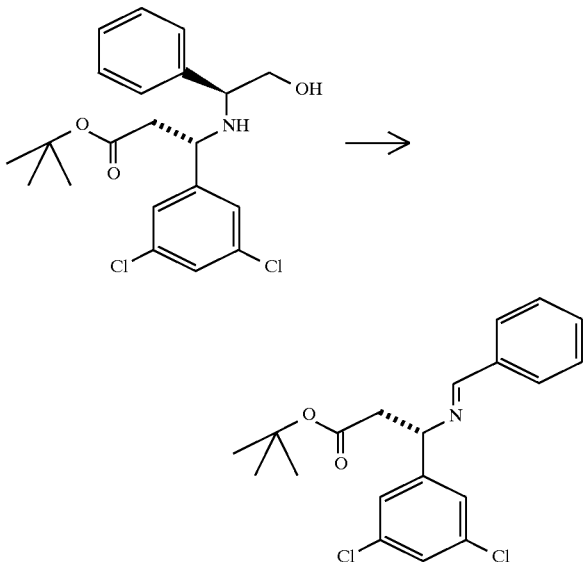

A solution of crude ester from Example 8 in EtOH (140 ml) was charged to a 500 ml round bottom 3N flask. A solution of methyl amine (8.9 ml, 0.1 mole) was added. A slurry of $NaIO_4$ (0.112 mole, 25.92 g) in $H_2O$ (72 ml) at 25° C. was added by portion while maintaining a temperature of 30° C. (±2° C.). The reaction was monitored by TLC. The reaction mixture was then stirred at room temperature for 15 hours. $NaIO_4$ (6 g, 0.026 mole) solid was added. After 4 hours, $NaIO_4$ (6 g, 0.026 mole) solid was added and the mixture was heated at 30° C. for 0.5 hour. After cooling to 25° C., the reaction mixture was concentrated under reduced pressure (water aspirator). MTBE was added and the mixture was filtered through a coarse glass fritted filter. The layers were separated and the organic layer was washed with $H_2O$ (100 ml) dried with $MgSO_4$ (25 g), filtered and concentrated under reduced pressure to afford 30.2 g of an orange oil containing compound 3a.

EXAMPLE 10

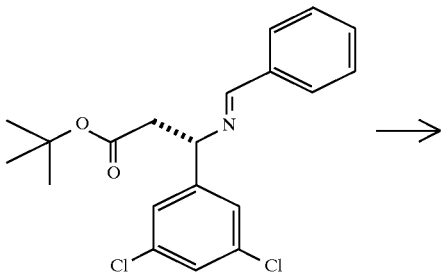

-continued

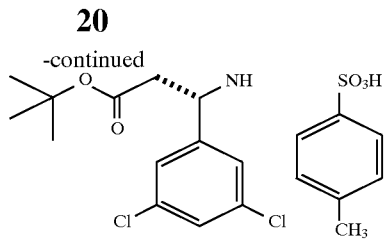

The crude mixture containing 3a was diluted with THF (65 ml) and was charged in a 500 ml round bottom 3N flask fitted with a mechanical stirrer and an addition funnel. A solution of p-toluenesulfonic acid monohydrate (13.6 g, 71.6 mmole) in THF (20 ml) was then added in 2 minutes followed by a wash of THF (5 ml) via the addition funnel. After 5 minutes, heptane (65 ml) was added and heavy precipitation occurred. Additional heptane (65 ml) was added. After 0.5 hour, the slurry was filtered through a coarse glass fritted pressure filter and was washed with heptane/THF 20% (100 ml) and heptane/THF 33% (150 ml). The cake was then dried under vacuum/nitrogen for 2 hours. The ivory solid 4a was collected to afford 25.1 g (63% overall yield from example 7) of the desired compound. $^1H$ NMR ($CDCl_3$, TMS) (ppm) 1.26 (s, 9H), 3.37 (s, 3H), 2.84 (dd, (AB), J=9.5, 16.3 Hz), 2.98 (dd, (AB), J=5.2, 16.2 Hz), 4.53 (m, 1H), 7.14 (d, 2H, J=7.9 Hz), 7.19 (t, 1H, J=1.8 Hz), 7.32 (d, 2H, J=8.1 Hz), 7.56 (d, 2H, J=8.1 Hz), 8.43 (s(broad), 3H); $^{13}C$ NMR ($CDCl_3$, TMS) δ(ppm): 21.37, 27.80, 39.47, 51.36, 81.85, 125.77, 126.43, 129.01, 129.06, 135.17, 139.14, 140.59, 140.69, 168.06. DSC: 120.30° C. (80.71 J/Kg), 242.63 (endothermic, 100.3 J/g) $[\alpha]^P_{25}$ = +37.4 (c=0.147, $CHCl_3$); IR (MIR) (cm-1) 1726, 1587, 1567.

Microanalytical: found for $C_{20}H_{25}Cl_2NO_2S$: C: 51.65; H: 5.64; N: 3.01; Cl: 15.13; S: 7.00 Calcd: C: 51.95; H: 5.45; N: 3.03; Cl: 15.33; S: 7.02.

EXAMPLE 11

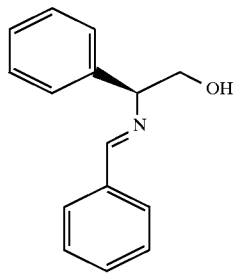

Following the general procedure for the preparation of imine described in Example 7 the compound 1b was prepared from S-phenyl glycinol (27.44 g, 0.2 mole), benzaldehyde (21.75 g, 0.205 mole) in toluene (200 mL) and $MgSO_4$ (8.0 g). The crude mixture was slurried in heptane (100 mL) and filtered to afford the compound 1b as a white solid (40.07 g, 88.9%).

EXAMPLE 12

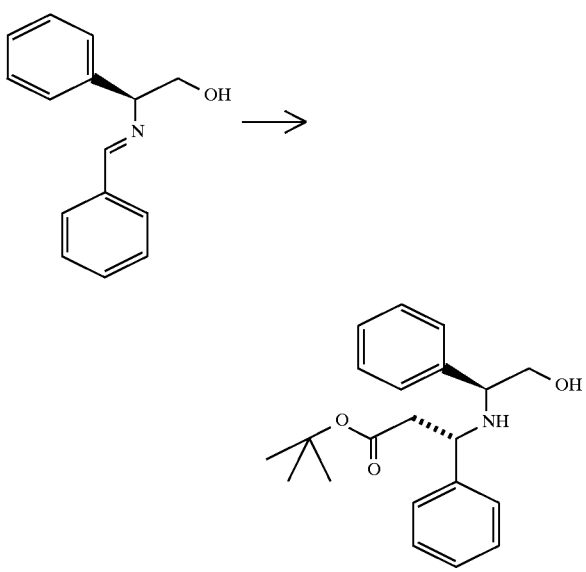

Following the general procedure for the Reformatsky coupling described in Example 8, compound 2b was prepared from a solution of Reformatsky reagent from Example 2 (1.38M in NMP/THF(3/2), 0.22 mole, 160 mL) and imine 1c (22.53 g, 0.1 mole) in NMP (20 mL) to afford a yellow oil (33.24 g, 97.3%) containing the compound 2b as a single diastereoisomer (as determined by $^1$H NMR and GC). The crude product was not purified and was used directly in the next step.

A sample of the crude product was purified by chromatography (SiO$_2$, 300 g), elution heptane/EtOAc 40%) to afford the desired compound as a pale yellow oil. $^1$H NMR (CDCl$_3$, TMS) δ(ppm) 1.40 (s, 9H), 2.60 (dd, 1H (AB), J=5.8, 15.3 Hz), 2.67 (dd, 1H (AB), J=8.515 4Hz), 3.58 (dd, 1H, J=6.2, 10.9 Hz), 3.71 (dd, 1H, J=6.3, 4.4), 3.84 (dd, 1H, J=4.3, 10.9 Hz), 4.19 (dd, 1H (AB), J=5.8, 8.3 Hz), 7.18 to 7.29 (m, 10H); $^{13}$C NMR (CDCl$_3$, TMS) δ(ppm):28.01, 43.54, 57.39, 61.21, 80.90, 126.92, 127.17, 127.34, 127.37, 128.44, 128.47, 141.61, 142.60, 171.25;

DSC:226.60° C. (endo. 113.1 J/g); $[\alpha]^P_{25}$ =+19.5° C. (c=1.2, CHCl$_3$); IR (MIR) (cm−1) 1720.

Microanalytical: calcd for C$_{21}$H$_{27}$NO$_3$: C: 73.87; H: 7.97; N: 4.10 Found: C: 73.87; H: 7.94; N: 3.97.

EXAMPLE 13

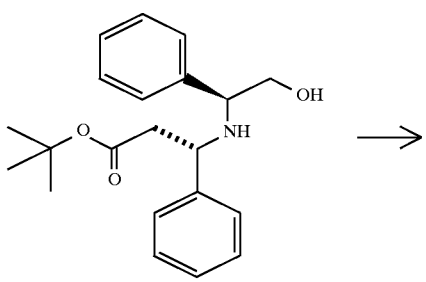

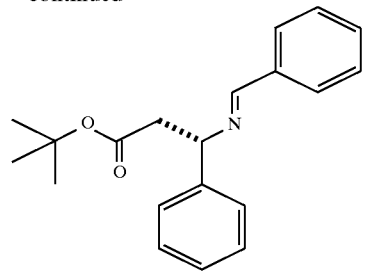

Following the general procedure for the oxidative cleavage as described in Example 9, the imine 3b, was prepared from NaIO$_4$ (19.57 g, 0.091 mole) and methyl amine (40 wt % in H$_2$O, 5.56 mL, 0.77 mole), and amino alcohol (27.37 g, 0.075 mole, crude) in ethanol (105 mL), H$_2$O (65 mL) (17 hours). After work up and concentration, a crude mixture (19.8 g) was obtained containing the phenyl imine 3b.

EXAMPLE 14

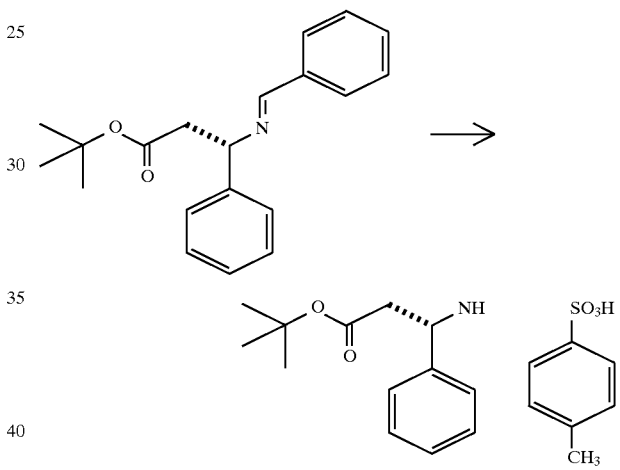

The phenyl imine 3b of Example 13 was hydrolyzed in THF (50 mL) following the general procedure for the preparation of PTSA salt described in Example 10 with a solution of PTSA.H$_2$O (10.72 g, 0.057 mole) in THF (15 mL). Heptane (100 mL) was added and the mixture heated to 35° C. for 30 minutes followed by slow cooling to 0° C. Filtration and washes with THF 30%/heptane (100 mL) afforded the desired salt 4b (19.28 g, 49% overall yield from Example 12) as an ivory solid.

$^1$H NMR (DMSO D6, TMS) δ(ppm) 1.26 (s, 9H), 2.29 (s, 3H), 2.81 (dd, 1H, J=9.2, 15.6 Hz) 2.99 (dd, 1H, J=5.8, 15.8 Hz), 4.55 (m, 1H), 7.11 (d, 2H, 7.8 Hz), 7.38 to 7.49 (m, 8H), 8.31 (s(broad), 3H); $^{13}$C NMR (DMSO D6, TMS) δ(ppm): 20.77, 27.45, 51.20, 80.84, 125.48, 127.69, 128.18, 128.58, 128.88, 136.41, 138.06, 145.00, 168.05.

DSC:107.62° C. (endo 177.9 J/Kg), 161.73 (endo, 2.77 J/g), 174.49 (endo 9.54 J/g), 236.51 (endo 354.2 J/g) $[\alpha]^P_{25}$ = −2.50 (c=0.91, CHCl$_3$); IR (MIR) (cm−1) 1725.

Microanalytical: calcd for C$_{20}$H$_{27}$NO$_5$S: C: 61.05; H: 6.92; N: 3.56; S: 8.15 found: C: 60.13; H: 7.03; N: 3.53; S: 8.46.

MS-CDI/NH$_3$/CH$_4$ M+2 223, M+1 222, 166, 149, 106.

EXAMPLE 15

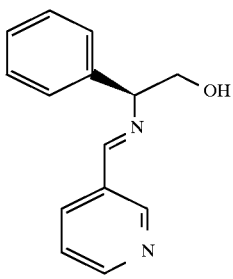

Following the general procedure for the preparation of imine described in Example 7, compound 1c was prepared from S-phenyl glycinol (27.44 g, 0.2 mole), 3-pyridinecarboxaldehyde (21.96 g, 0.205 mole) in toluene (120 mL) with $MgSO_4$ (8 g). The crude imine was slurried in heptane (100 mL), stirred for 2 hours and filtered to afford 42.25 g (93.3% yield) of the imine 1c as a white powder.

EXAMPLE 16

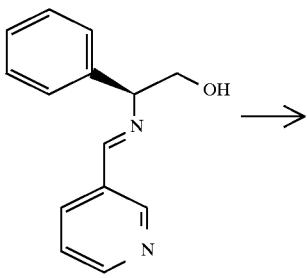

Following the general procedure for the Reformatsky coupling described in Example 8, compound 2c was prepared from a solution of Reformatsky reagent of Example 2 (1.36 M in NMP/THF(3/2), 0.164 mole, 121 mL) and imine 1c from Example 15 (17.0 g, 0.075 mole) in NMP (20 m). Regular extraction yielded 17 g of a crude mixture. Additional extractions were performed. A saturated solution of ammonium chloride (50 mL) was added to the aqueous layer followed by MTBE extraction. This procedure was repeated. The MTBE layers were combined and washed as in the general procedure to yield an additional 10.35 g of a crude mixture. The crude mixtures were combined to afford 27.85 g (25.69 g, 100%) of an orange oil containing the compound 2c as a single diastereoisomer (as determined by $^1H$ NMR and GC). The crude product was not purified and was used directly in the next step.

A sample of crude product was purified by chromatography ($SiO_2$, 50 g), elution heptane/EtOAc 60%) and recrystallized from MTBE/heptane (4/1) to afford the desired compound as a white solid. $^1H$ NMR ($CDCl_3$, TMS) δ(ppm) 1.38 (s, 9H), 2.60 (dd(AB), 1H, J=5.7, 15.6 Hz), 2.71 (dd(AB), 1H, J=8.1, 15.5 Hz), 3.60 (dd(AB), 1H, J=6.8, 10.5 Hz), 3.72 to 3.80 (m, 2H), 4.20 (dd, 1H, J=5.8, 8.1 Hz), 7.13 to 7.23 (m, 6H, (aromatic)), 7.62 (dt, 1H, J=1.8, 8.0 Hz), 8.46 (dd, 1H, J=1.6, 5.0 Hz), 8.54 (d, 1H, J=1.9 Hz); $^{13}C$ NMR ($CDCl_3$, TMS) δ(ppm): 26.72, 27.75, 27.84, 42.46, 55.59, 62.83, 66.10, 81.07, 123.58, 127.16, 127.25, 128.17, 136.11, 139.40, 140.66, 147.60, 148.32, 170.19; DSC: 85.75° C. (endo. 133.4 J/g); $[\alpha]^D_{25} = \pm 17.30°$ (c=1.035, $CHCl_3$); IR (MIR) (cm−1) 1718. UV max (nm)=205 (abs= 0.48), 261 (abs=0.096), 268 (abs=0.073)

Microanalytical: calcd for $C_{20}H_{26}N_2O_3$: C: 70.15; H: 7.65; N: 8.18 Found: C: 70.24; H: 7.79; N: 8.02.

EXAMPLE 17

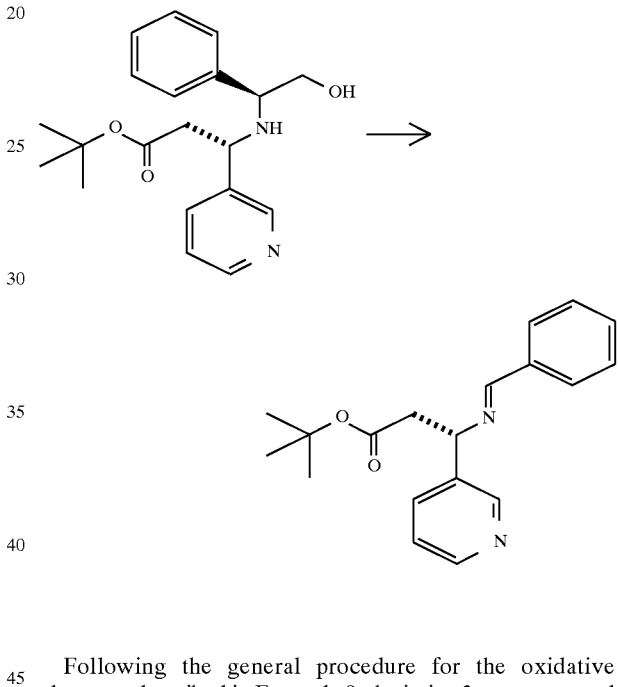

Following the general procedure for the oxidative cleavage, described in Example 9, the imine 3c was prepared from $NaIO_4$ (19.57 g, 0.091 mole), methyl amine (40 wt % in $H_2O$, 5.56 mL, 0.77 mole), and amino alcohol 2c (27.37 g, 0.075 mole, crude) in ethanol (105 mL), $H_2O$ (65 mL) (17 hours). After work up and concentration, a crude product (19.8 g) was obtained containing the phenyl imine 3c.

EXAMPLE 18

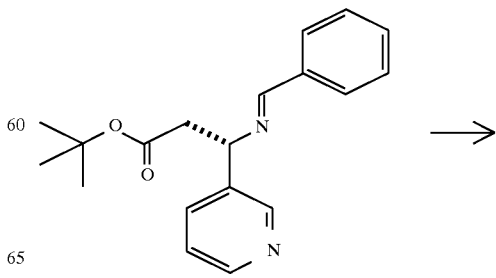

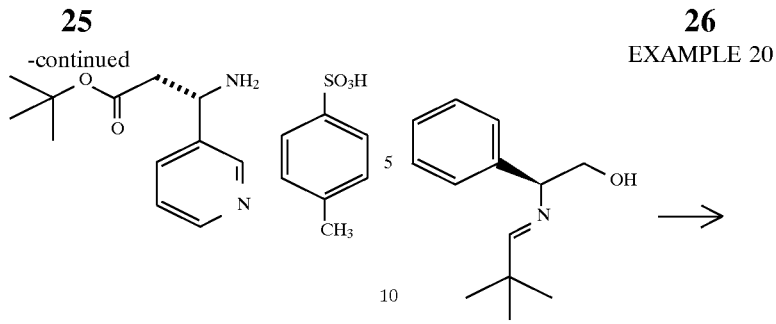

The phenyl imine 3c was hydrolyzed in THF (50 mL) following the general procedure for the formation of PTSA salt described in Example 10 with a solution of PTSA:H$_2$O (10.72 g, 0.057 mole) in THF (15 mL). Heptane (100 mL) was added and the mixture heated to 35° C. for 30 minutes followed by slow cooling to 0° C. Filtration and wash with THF 30%/heptane (100 mL) afforded the desired salt 4c (19.28 g, 65% overall yield from Example 16) as an ivory solid.

$^1$H NMR (CDCl$_3$, TMS) δ(ppm) 1.24 (s, 9H), 2.35 (s, 3H), 2.90 (dd, 1H, (AB), J=8.87, 16.6 Hz), 3.09 (dd, 1H (AB), J=5.8, 16.6 Hz), 4.71 (dd, 1H, J=6.0, 8.9 Hz), 7.09 (d, 2H, J=7.9 Hz), 7.19 (dd, 1H, J=4.9, 7.9 Hz), 7.57 (d, 2H, J=8.1 Hz), 7.99 (dd, 1H, 1.7, 8.1 Hz), 8.46 (dd, 1H, J=1.4, 5.0 Hz), 8.70 (d, 1H, 1.9 Hz); $^{13}$C NMR (CDCl$_3$, TMS) δ(ppm) : 21.30, 27.72, 38.99, 49.86, 81.95, 124.16, 125.84, 128.95, 132.52, 137.18, 140.46, 141.22, 148.28, 148.57, 168.34. DSC: 113.62° C. (endo 68.41 J/Kg), 159.9 (endo, 62.88 J/g) [α]$^D_{25}$ =−1.5 (c=0.998, CHCl$_3$);

IR (MIR) (cm−1) 2116, 1721, 1540.

Microanalytical: found for C$_{19}$H$_{26}$N$_2$O$_5$S: C: 57.85; H: 6.64; N: 7.10; S: 8.13 calcd: C: 57.15; H: 6.46; N: 6.44; S: 8.38.

MS-CDI/NH$_3$/CH$_4$ M+2 224, M+1 223, 195, 167, 150, 107.

EXAMPLE 19

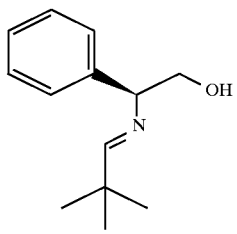

Following the general procedure for the preparation of imine described in Example 7, compound 1e was prepared from L-phenylglycinol (10.00 g, 0.073 mole) and trimethylacetaldehyde (6.59 g, 0.076 mole) in toluene (50 mL) with MgSO$_4$ as drying agent (2.7 g) to afford imine 1e (14.41 g) as a clear oil which was used in the following Example without further purification.

EXAMPLE 20

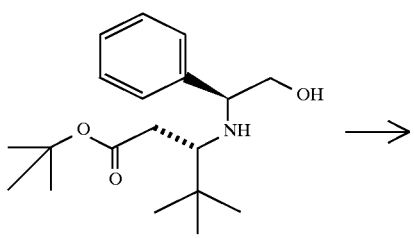

A solution of the imine 1e in DMSO (30 mL) was added in 15 minutes to a solution of Reformatsky reagent from Example 2 (57.50 g, 0.173 mole) in DMSO (80 mL) while cooling to 8° C. After addition the mixture was held at 22° C. and stirred for 22 hours. Reformatsky reagent from Example 2 (23.00 g, 0.069 mole) was then added as a solid. The mixture was stirred at 22° C. for an additional 8 hours (89% conversion by GC). A saturated aqueous solution of NH$_4$Cl (100 mL) was then added and the mixture extracted with MTBE (2×100 mL). The organic layers were combined, washed with a saturated solution of NH$_4$Cl (100 mL), H$_2$O (100 mL), brine (100 mL) and dried with Na$_2$SO$_4$. Filtration and concentration afforded a crude mixture of yellow oil (17.57 g) containing the compound 2e which was used without purification in the following Example. A sample of product was purified by chromatography (SiO$_2$, 300 g), elution heptane/EtOAc 40%) to afford the desired compound as a pale yellow oil. $^1$H NMR (CDCl$_3$, TMS) δ(ppm) 0.83 (s, 9H), 1.46 (s, 9H), 2.24 (dd(AB), 1H, J=5.4, 15.4 Hz), 2.51 (dd(AB), 1H, 5.3, 15.5 Hz), 2.67 (t, 1H, J=5.4 Hz), 3.53 (dd(AB), 1H, J=9.0, 10.8 Hz), 3.67 (dd, 1H, J=4.3, 10.8 Hz), 3.85 (dd, J=4.27, 8.8 Hz), 7.23 to 7.34 (m, 5H); $^{13}$C NMR (CDCl$_3$, TMS) δ(ppm):26.68, 28.06, 35.04, 37.87, 60.80, 62.73, 67.33, 80.48, 127.42, 127.75, 128.35.

Microanalytical: calcd for C$_{19}$H$_{31}$NO$_3$: C: 70.99; H: 9.72; N: 4.36 Found: C: 69.91; H: 9.98; N: 4.15.

EXAMPLE 21

EXAMPLE 23

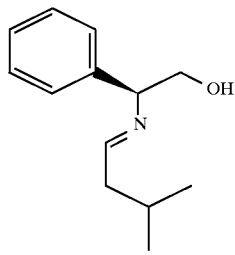

Following the general procedure for the preparation of imine described in Example 22, compound 1f was prepared from L-phenylglycinol (10.00 g, 0.073 mole) and isobutyraldehyde (6.59 g, 0.076 mole) in toluene (50 mL) with MgSO$_4$ as drying agent (2.9 g) to afford 15.40 g of imine 1f as a yellow oil which was used without further purification in the following Example.

EXAMPLE 24

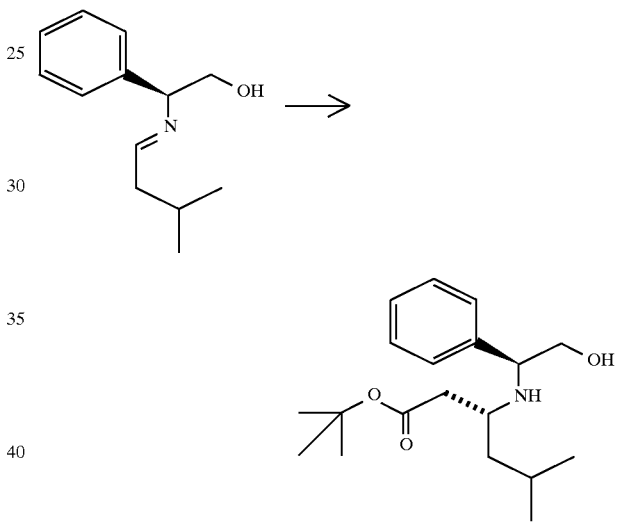

A solution of the imine 1f produced in Example 23 in DMSO (30 mL) was added over 15 minutes to a solution of Reformatsky reagent from Example 2 (57.50 g, 0.173 mole) in DMSO (80 mL) while cooling to 8° C. The mixture was held at 22° C. and stirred for 16 hours. Additional Reformatsky reagent from Example 2 (2.50 g, 0.008 mole) was then added as a solid and the mixture was stirred at 22° C. for an additional 4 hours (92% conversion by GC). A saturated aqueous solution of NH$_4$Cl (100 mL) was then added and the mixture extracted with MTBE (2×100 mL). The organic layers were combined, washed with a saturated solution of NH$_4$Cl (100 mL), H$_2$O (100 mL), brine (100 mL) and dried with Na$_2$SO$_4$. Filtration and concentration afforded (20.1 g, 85.65% overall yield from Example 23) a yellow oil containing the compound 2f which was used without further purification. A sample of product was purified by chromatography (SiO$_2$, 300 g), elution heptane/ EtOAc 40%) to afford the desired compound 2f as a pale yellow oil. 1H NMR (CDCl$_3$, TMS) δ(ppm) 0.68 (d, 3H, J=6.5 Hz), 0.83 (2H, J=6.6 Hz), 1.19 (m, 1H), 1.32 (m, 1H), 1.46 (s, 9H), 1.61 (s, 1H), 2.26 (dd(AB), 1H, J=5.70, 14.62 Hz), 2.38 (dd(AB), 1H, J=5.71, 14.57 Hz), 2.92 (m, 1H), 3.51 (dd(AB), 1H, J=10.75, 8.54 Hz), 3.69 (dd(AB), 1H, -continued

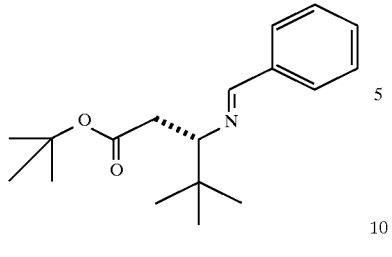

The crude product containing compound 3e from Example 20 was diluted with MeOH (520 mL), cooled to 0° C. and Pb(OAc)$_4$ (23.40 g, 0.0536 mole) was added. The resulting orange solution was stirred for 1 hour at 0° C. A 15% aqueous solution of NaOH (100 mL) was added and the mixture was held at 22° C. and concentrated under reduced pressure to remove MeOH. MTBE was added, the mixture filtered and the layers were separated. The organic layer was dried with NaSO$_4$, filtered and concentrated to afford 14.30 g of a yellow oil containing 3e.

EXAMPLE 22

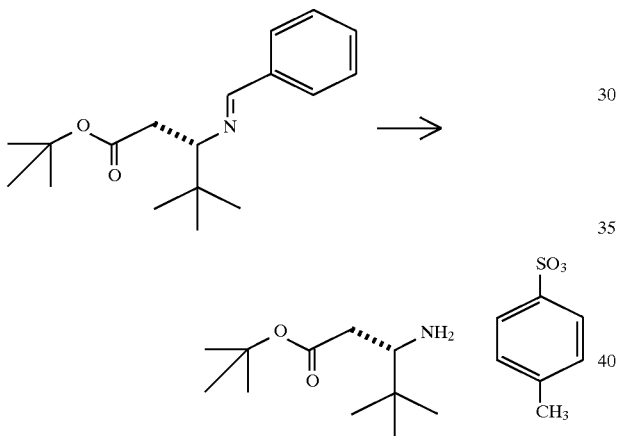

The crude oil containing 3e from Example 21 was dissolved in MTBE (38 mL) and paratoluene sulfonic acid (8.24 g, 0.043 g) was added. After 15 minutes, heptane (150 mL) was added and the resultant slurry was filtered to afford 13.86 g of a white solid containing the salt with some impurities. The compound was purified by reslurrying in MTBE/heptane followed by filtration under nitrogen/ vacuum (pressure filter) to yield 11.83 g of product 4e (43.4% overall yield from Example 19).

$^1$H NMR (CDCl$_3$, TMS) δ(ppm) 1.01 (s, 9H), 1.41 (s, 1H), 2.35 (s, 3H), 2.55 (dd, 1H, J=4.0, 17.7 Hz), 2.66 (dd, 1H, J=9.0, 17.6 Hz), 3.28 (m, 1H), 7.15 (d, 2H), 7.75 (d, 2H), 7.80 (s(broad), 3H); $^{13}$C NMR (DMSO D6, TMS) δ(ppm): 21.28, 26.00, 27.92, 33.22, 33.83, 57.38, 82.12, 126.08, 128.70, 139.92, 141.98, 170.96 DSC: 117.11° C. (endo 65.14 J/Kg), 147.84° C. (endo 93.35 J/g); [α]$^D_{25}$ =−24.7° (c=0.777, CHCl$_3$); IR (MIR) (cm-1) 1718.

Microanalytical: calcd for C$_{18}$H$_{31}$NO$_5$S: C: 57.88; H: 8.37; N: 3.75; S: 8.58 Found: C: 57.64; H: 8.46; N: 3.58; S: 8.80.

J=4.32, 10.72 Hz), 3.84 (dd, 1H, J=8.49, 4.44 Hz), 7.23 to 7.35 (m, 5H); $^{13}$C NMR (CDCl$_3$, TMS) δ(ppm):22.26, 22.94, 24.68, 28.13, 40.41, 44.95, 50.47, 61.77, 67.00, 80.55, 127.29, 127.49, 128.50, 141.51, 171.96. DSC: 171.62° C. (endo. 36.3 J/g), 224.06° C. (234.5 J/g), 281.65° C. (endo 234.5 J/g); $[\alpha]^D{}_{25}$ =+49° (c=1.005, CHCl$_3$); IR (MIR) (cm−1) 3428, 3331, 1721.

Microanalytical: calcd for C$_{19}$H$_{31}$NO$_3$: C: 70.99; H: 9.72; N: 4.36 Found: C: 69.29; H: 9.75; N: 4.08.

EXAMPLE 25

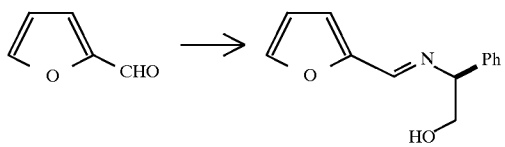

Freshly distilled 2-furaldehyde (26.73 g; 0.278 moles) was dissolved in toluene (100 mL) under nitrogen in a 500 mL 3-neck flask with magnetic stirring. A thermocouple thermometer was put in place. L-phenylglycinol (38.16 g; 0.278 mole) was added. The mixture was stirred for 30 minutes with ice cooling. Magnesium sulfate (33.5 g; 0.278 moles) was added. After stirring a further 30 minutes the magnesium sulfate was removed by filtration. The solvent was removed by rotary evaporation. Heptane (100 mL) was added with stirring. The resulting yellow solid was dried under vacuum (54.72 g; 91.4%).

$^1$H NMR (400 MHz, CDCl$_3$) δ8.17 (s, 1H), 7.54 (d, J=1.75 Hz), 7.43–7.25 (m, 5H), 6.78 (dd, J=3.4, 0.7 Hz, 1H), 6.48 (dd, J=3.4, 1.8 Hz, 1H), 4.43 (dd, J=8.6, 4.5 Hz, 1H), 4.03 (dd, J=11.3, 8.6 Hz, 1H), 3.90 (dd, J =11.3, 4.4 Hz, 1H). $^{13}$C NMR (CDCl$_3$) δ151.52, 151.16, 144.99, 140.42, 128.61, 127.51, 127.32, 114.91, 111.75, 77.19, 67.50 ppm. IR v 3257, 2956, 2920, 2885, 2858, 1649, 1486, 1473, 1448, 1415, 1393, 1367, 1280, 1152, 1077, 1054, 1023, 931, 883, 746, 701 cm$^{-1}$. $[\alpha]_{589}$=−99.7° (c 1.008, CHCl$_3$).

Analysis Calculated for C$_{13}$H$_{13}$NO$_2$: C: 72.54; H: 6.09; N: 6.51 Found: C: 72.57; H: 6.34; N: 6.51.

EXAMPLE 26

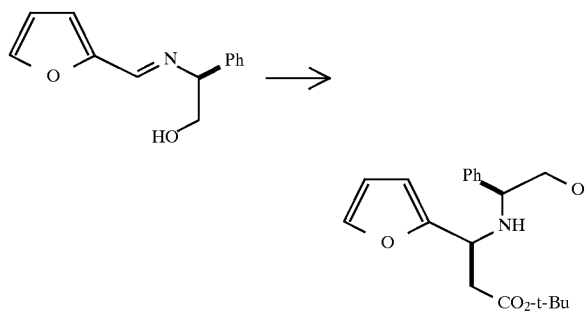

A solution of t-butyl(bromozinc)acetate from Example 2 in N-methylpyrrolidinone (43 mL of a 1.36M solution; 58.07 mmol) was charged to a 250 mL 3-neck flask under nitrogen. Overhead mechanical stirring and a cooling bath with automated temperature control were put in place. The solution was cooled to −5° C. A solution of the imine from Example 25 (5.00 g; 23.23 mmol) in NMP (40 mL) was added via addition funnel. After stirring for 3.5 hours the mixture was quenched by addition of 2N hydrochloric acid (30 mL) and saturated aqueous ammonium chloride solution (60 mL). The mixture was extracted with MTBE (2×100 mL). The combined extracts were washed with ammonium chloride solution (50 mL), water (50 mL) and sodium chloride solution (50 mL). The solution was dried (Na$_2$SO$_4$) and the solvent was removed under vacuum. The crude product (yellow oil, 7.3 g) was purified by column chromatography on silica, eluting with heptane/MTBE (2:1) to yield the desired product (5.43 g; 70.5%).

$^1$H NMR (400 MHz, CDCl$_3$) δ(ppm): 7.29–7.19 (m, 6H), 6.21 (dd, J=3.2, 1.8 Hz, 1H), 6.07 (d, J=3.2 Hz, 1H), 4.25 (dd, J=7.7, 6.2 Hz, 1H), 3.79–3.75 (m, 2H), 3.55 (dd, J=12.0, 7.9 Hz, 1H), 2.71–2.65 (m, 2H), 1.44 (s, 9H). $^{13}$C NMR (CDCl$_3$) δ(ppm): 170.96, 155.28, 141.62, 141.44, 128.43, 127.39, 127.08, 109.94, 106.29, 81.01, 66.09, 61.69, 51.41, 40.74, 28.03. IR v 3427, 2974, 2929, 2870, 1720, 1452, 1365, 1147 cm$^{-1}$. $[\alpha]_{589}$=7.6° (c 0.983, CHCl$_3$).

EXAMPLE 27

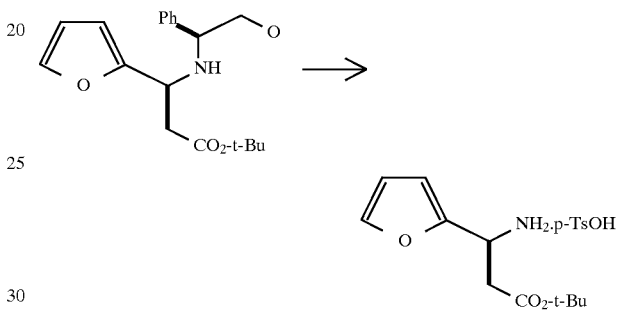

The aminoalcohol from Example 26 (4.88 g; 14.72 mmol) was dissolved in ethanol (30 mL) in a 100 mL 3-neck flask with magnetic stirring under nitrogen. Methylamine (1.30 mL of a 40% aqueous solution; 15.1 mmol) was added via syringe. A solution of sodium periodate (3.55 g; 16.6 mmol) in water (24 mL) at 30° C. was added in portions. Ice cooling was employed to keep the reaction temperature below 30° C. The reaction mixture was stirred for 2 hours at 25° C. then cooled to 0° C., The mixture was filtered through a glass frit washing with MTBE (100 mL). The filtrate was washed with water (50 mL) and sodium chloride solution (50 mL). The combined aqueous phases were extracted with MTBE (50 mL). The extract was washed with sodium chloride solution (30 mL). The combined organic phases were dried (Na$_2$SO$_4$) and the solvent was removed under vacuum to yield a crude orange oil (4.10 g). This was dissolved in THF (10 mL) and added to p-toluenesulfonic acid (2.35 g; 12.33 mmol) at 0° C. with stirring. Heptane (25 mL) was added causing some material to oil out of solution. Further heptane (25 mL) was added and stirring continued until the material solidified. The material was broken up, collected by filtration, washed with heptane/THF (3:1, 20 mL) to yield a pale yellow solid (4.39 g; 78%).

$^1$H NMR (400 MHz, CDCl$_3$) δ(ppm): 8.23 (br, s, 3H), 7.67 (d, J=8.1 Hz, 2H), 7.23–7.22 (m, 1H), 7.12 (d, J=8.0 Hz, 2H), 6.40 (d, J=3.4 Hz, 1H), 6.22 (dd, J=3.3, 1.8 Hz, 1H), 4.72 (br, m, 1H), 2.96 (n, 2H), 2.35 (s, 3H), 1.32 (s, 9H). $^{13}$C NMR (CDCl$_3$) δ(ppm): 168.80, 148.60, 142.89, 141.45, 140.24, 128.80, 126.03, 110.60, 109.47, 81.74, 45.67, 36.77, 27.83, 21.31.

Analysis Calculated for C$_{18}$H$_{25}$NO$_6$S.1/2H$_2$O: C: 55.09; H: 6.42; N: 3.57 Found: C: 55.08; H: 6.69; N: 3.83.

What is claimed is:

1. A process for the preparation of a chiral β-amino acid of the formula 5,840,961

31

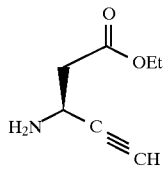

which comprises treating 3-(trimethylsilyl)-2-propynal with L-phenylglycinol to produce αS-[[3-(trimethylsilyl)-2-propynylidene]amino]benzene-ethanol; reacting αS-[[3-(trimethylsilyl)-2-propynylidene]amino]benzenethanol with BrZnCH₂CO₂t-Bu to produce 1,1-dimethylethyl 3S-[(2-hydroxy-1S-phenylethyl)amino]-5-(trimethylsilyl)-4-pentynoate; reacting 1,1-dimethylethyl 3S-[(2-hydroxy-1S-phenylethyl)amino]-5-(trimethylsilyl)-4-pentynoate with sodium periodate to form 1,1-dimethylethyl 3S-[(phenylmethylene)amino]-5-(trimethylsilyl)-4-pentynoate; hydrolyzing 1,1-dimethylethyl 3S-[(phenylmethylene)amino]-5-(trimethylsilyl)-4-pentynoate to produce 1,1-dimethylethyl 3S-amino-5-(trimethylsilyl)-4-pentynoate; transesterifying 1,1-dimethylethyl 3S-amino-5-(trimethylsilyl)-4-pentynoate and desilylating to produce ethyl 3S-amino-4-pentynoate.

2. The process according to claim 1 wherein the 3-(trimethylsilyl)-2-propynal is treated with L-phenylglycinol in toluene.

3. The process according to claim 1 wherein the αS-[[3-(trimethylsilyl)-2-propynylidene]amino]benzenethanol is reacted with BrZnCH₂CO₂t-Bu in THF/NMP.

4. The process according to claim 1 wherein the 1,1-dimethyl 3S-[(2-hydroxy-1-S-phenylethyl)amino]-5-(trimethylsilyl)-4-pentynoate is reacted with sodium periodate in the presence of methylamine in ethanol/water.

5. The process according to claim 1 wherein 1,1-dimethylethyl 3S-[(phenylmethylene)amino]-5-(trimethylsilyl)-4-pentynoate is hydrolyzed in the presence of para-toluenesulfonic acid in MTBE, THF or toluene.

6. A process for the preparation of an (R) β-amino acid of the formula

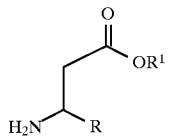

wherein R is selected from the group consisting of alkynyl, alkenyl, lower alkyl, aryl, substituted aryl, pyridyl and furanyl; and R¹ is alkyl; comprising treating an aldehyde of the formula

with (R) phenylglycinol in tetrahydrofuran or toluene to produce an imino alcohol of the formula

32

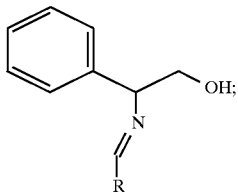

reacting said imino alcohol with BrZnCH₂CO₂-t-Bu in NMP, DMSO, THF or NMP/THF followed by addition of acidic ammonium chloride/HCl or basic ammonium hydroxide to give an amino alcohol of the formula

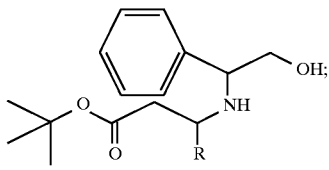

reacting said amino alcohol with NaIO₄ in the presence of methyl amine in ethanol/water or lead tetraacetate in methanol to form an imine of the formula

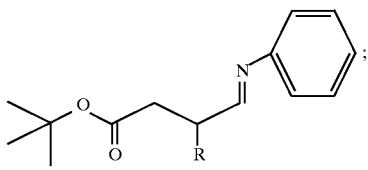

and hydrolyzing said imine in the presence of para-toluenesulfonic acid to produce an (R)-amino acid of the formula

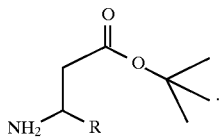

7. The process according to claim 6 wherein R is phenyl.
8. The process according to claim 6 wherein R is 3,5-dichlorophenyl.
9. The process according to claim 6 wherein R is 3-pyridinyl.
10. The process according to claim 6 wherein R is 2-furanyl.
11. The process according to claim 6 wherein R is t-butyl.
12. The process according to claim 6 wherein R is isopropyl.
13. A process for the preparation of an (S) β-amino acid of the formula

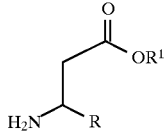

wherein R is selected from the group consisting of alkynyl, alkenyl, lower alkyl, aryl, substituted aryl, pyridyl and furanyl; and R¹ is alkyl; comprising treating an aldehyde of the formula

with (S) phenylglycinol in tetrahydrofuran or toluene to produce an imino alcohol of the formula

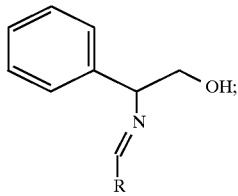

reacting said imino alcohol with BrZnCH₂CO₂-t-Bu in NMP, DMSO, THF or NMP/THF followed by addition of acidic ammonium chloride/HCl or basic ammonium hydroxide to give an amino alcohol of the formula

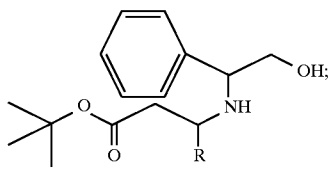

reacting said amino alcohol with NaIO₄ in the presence of methyl amine in ethanol/water or lead tetraacetate in methanol to form an imine of the formula

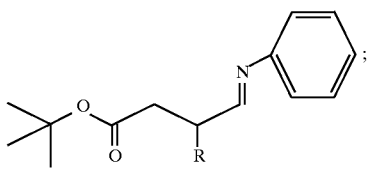

and hydrolyzing said imine in the presence of para-toluenesulfonic acid to produce an (S)-amino acid of the formula

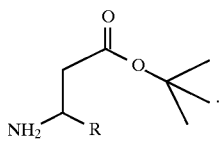

14. The process according to claim 13 wherein R is phenyl.

15. The process according to claim 13 wherein R is 3,5-dichlorophenyl.

16. The process according to claim 13 wherein R is 3-pyridinyl.

17. The process according to claim 13 wherein R is 2-furanyl.

18. The process according to claim 13 wherein R is t-butyl.

19. The process according to claim 13 wherein R is isopropyl.

* * * * *